(12) United States Patent
Lee

(10) Patent No.: US 10,849,825 B2
(45) Date of Patent: Dec. 1, 2020

(54) INFUSION FLOW-RATE REGULATING DEVICE

(71) Applicant: Hanvit MD Co., Ltd, Daejeon (KR)

(72) Inventor: Doo Yong Lee, Daejeon (KR)

(73) Assignee: Hanvit MD Co., Ltd, Daejeon (KR)

( * ) Notice: Subject to any disclaimer, the term of this patent is extended or adjusted under 35 U.S.C. 154(b) by 210 days.

(21) Appl. No.: 16/060,011

(22) PCT Filed: Aug. 1, 2017

(86) PCT No.: PCT/KR2017/008316
§ 371 (c)(1),
(2) Date: Jun. 6, 2018

(87) PCT Pub. No.: WO2018/026178
PCT Pub. Date: Feb. 8, 2018

(65) Prior Publication Data
US 2018/0360688 A1  Dec. 20, 2018

(30) Foreign Application Priority Data

Aug. 3, 2016 (KR) ........................ 10-2016-0099192
Nov. 23, 2016 (KR) ........................ 10-2016-0156903
May 26, 2017 (KR) ........................ 10-2017-0065064

(51) Int. Cl.
*A61J 1/10*   (2006.01)
*A61J 1/22*   (2006.01)
(Continued)

(52) U.S. Cl.
CPC . *A61J 1/10* (2013.01); *A61J 1/22* (2013.01); *A61M 5/14* (2013.01); *A61M 5/168* (2013.01);
(Continued)

(58) Field of Classification Search
CPC .... A61J 1/10; A61J 1/22; A61M 5/14; A61M 5/168; A61M 5/16818; A61M 5/172;
(Continued)

(56) References Cited

U.S. PATENT DOCUMENTS 4,820,281 A * 4/1989 Lawler, Jr. .......... A61M 5/1689
604/253
6,129,702 A * 10/2000 Woias ................... A61M 5/141
604/250

(Continued)

FOREIGN PATENT DOCUMENTS

| KR | 10-2006-0036622 A | 5/2006 |
|---|---|---|
| KR | 10-1487754 B1 | 1/2015 |
| KR | 10-1532613 B1 | 6/2015 |

OTHER PUBLICATIONS

International Search Report for International Patent Application No. PCT/KR2017/008316, dated Nov. 9, 2017.

*Primary Examiner* — Bhisma Mehta
*Assistant Examiner* — Daniel Moore

(57) ABSTRACT

The present invention relates to an infusion flow-rate regulating device capable of allowing easy attachment and detachment of a flow-rate regulator provided in an infusion solution set and of automatically adjusting a dial of the attached flow regulator such that a fluid is able to be administered at a target flow rate. To this end, the infusion flow-rate regulating device includes a main body, a dial mounting unit rotatably connected to the main body, a flow-rate regulator separation unit for preventing arbitrary separation of a flow-rate regulator mounted on the dial mounting unit, and a controller for controlling a flow rate of fluid.

13 Claims, 13 Drawing Sheets

(51) Int. Cl.
    *A61M 5/168*     (2006.01)
    *A61M 5/172*     (2006.01)
    *A61M 5/14*     (2006.01)

(52) U.S. Cl.
    CPC .... *A61M 5/16818* (2013.01); *A61M 5/16877* (2013.01); *A61M 5/16886* (2013.01); *A61M 5/172* (2013.01); *A61M 5/1684* (2013.01)

(58) Field of Classification Search
    CPC .......... A61M 5/16877; A61M 5/16886; A61M 5/1684; A61M 2205/3306; A61M 5/365; A61M 5/1689; A61M 5/16813; A61M 5/1409; A61M 5/1411; A61M 2205/3379
    See application file for complete search history.

(56) References Cited

U.S. PATENT DOCUMENTS

| | | |
|---|---|---|
| 7,887,520 B2 | 2/2011 | Simon |
| 2006/0004330 A1* | 1/2006 | Carlisle ............. A61M 5/14236 |
| | | 604/246 |
| 2012/0053556 A1 | 3/2012 | Lee |
| 2013/0345658 A1* | 12/2013 | Browne ............ A61M 5/16831 |
| | | 604/500 |

* cited by examiner

INFUSION FLOW-RATE REGULATING DEVICE

CROSS-REFERENCE TO RELATED APPLICATIONS

The present specification is a U.S. National Stage of International Patent Application No. PCT/KR2017/008316 filed Aug. 1, 2017, which claims priority to and the benefit of Korean Patent Application Nos. 10-2016-0099192, 10-2016-0156903, and 10-2017-0065064, filed in the Korean Intellectual Property Office on Aug. 3, 2016, Nov. 23, 2016, and May 26, 2017, respectively, the entire contents of which are incorporated herein by reference.

TECHNICAL FIELD

The present invention relates to an infusion flow-rate regulating device capable of allowing easy attachment and detachment of a flow-rate regulator provided in an infusion solution set and of automatically adjusting a dial of the attached flow-rate regulator such that infusion solution is able to be administered at a target flow rate.

BACKGROUND ART

As illustrated in FIG. 1, a typical infusion solution set 20 includes flow regulation means 24' and 24 mounted in the middle of a tube 22 for controlling a flow rate of the infusion.

As the flow regulation means 24' and 24, a roller clamp 24' for controlling a flow rate by operation of a roller and a flow-rate regulator 24 for controlling a flow rate by changing an internal passage have been widely used until recently.

However, since the flow rate of the infusion solution is changed depending on different conditions, such as a level difference H defined by the "difference in height between a level of fluid in an infusion solution bag 10 and an injection needle 23", a temperature of the infusion solution, and a patient's condition, it is impossible to control the flow rate of the infusion at a prescribed target flow rate by the flow regulation means 24' and 24 in the majority of cases. For this reason, there is a problem in that the flow rate of the infusion is controlled by trial & error while changing the roller or dial of the flow regulation means 24' and 24 little by little to observe a rate of an intravenous (IV) drop 21a (unit: gtt) with the naked eye in the actual clinical site.

Due to this problem, an infusion pump disclosed in Korean Utility Model Publication No. 20-1989-0004900 has been mainly used for precise injection of an infusion solution until recently.

The infusion pump is a device that forcibly deforms the outer surface of a tube using a pumping means for injection of an infusion solution at a target flow rate. Hence, the infusion pump may cause an issue such as a burst of blood vessels since a pressure is applied even when a patient's blood vessel is blocked during injection of the infusion solution. In addition, the infusion pump consumes a lot of power since it is operated by continuous supply of power and the injection of an infusion solution is stopped when the supply of power is stopped, which may lead to a medical accident. Hence, it is inconvenient since attention is always paid to the infusion pump. In addition, an exclusive infusion pump tube with high elastic restoring force should be used for injection of an infusion solution at an accurate flow rate. However, since the deformation of the tube is continuously repeated here as elsewhere, the injection of an infusion solution at the accurate flow rate may not be ensured when the tube is deformed due to a reduction in the elastic restoring force thereof.

Accordingly, there has been a need for an infusion flow-rate regulating device capable of accurately controlling a flow rate of the infusion using a typical infusion solution set while being usable with ease.

In order to resolve the demand in the clinical site, the inventor of the present invention devises an infusion flow-rate regulating device (Korean Patent No. 10-1532613) that includes a flow-rate regulator 30 mounted therein to calculate a single flow rate by rotating the dial of the flow-rate regulator 30 to an arbitrary initial rotational position and to control a flow rate by grasping the rotational position of the flow-rate regulator 30 corresponding to a target flow rate using the calculated flow rate and rotating the dial of the flow-rate regulator 30 to a target rotational position, as illustrated in FIG. 2.

However, as illustrated in FIG. 2, there is a problem in that it is difficult to miniaturize the structure of the infusion flow-rate regulating device 100, which grips and covers the flow-rate regulator 30 by a cover for operation, since it is generally complicated due to multiple operations when the flow-rate regulator 30 is mounted in the infusion flow-rate regulating device 100. In addition, the infusion flow-rate regulating device is problematic in that it may not measure and monitor an accurate flow rate within a typical vibration range.

PRIOR ART DOCUMENT

Patent Document (Patent document 1) KR 20-1989-0004900 Y1 (1989 Jul. 28.)
(Patent document 2) KR 10-1532613 B1 (2016 Jun. 30)

SUMMARY OF INVENTION

Technical Problem

An object of the present invention is to provide an infusion flow-rate regulating device capable of having a conveniently portable size in a clinical site, of allowing safe and rapid attachment and detachment of a flow-rate regulator 240 provided in an infusion solution set 200, and of accurately controlling an injection of an infusion solution flow rate at a target flow rate.

The present invention is not limited to the above-mentioned object, and other objects of the present invention can be clearly understood by those skilled in the art to which the present invention pertains from the following description.

Solution to Problem

To accomplish the object described above, the present invention provides an infusion flow-rate regulating device 100 for rotating a dial 242 of a flow-rate regulator 240 to control a flow rate of the infusion, the infusion flow-rate regulating device 100 including a main body 110 equipped with a drive motor (not shown) therein, a dial mounting unit 130 connected to the drive motor (not shown) and configured to mount and rotate the dial 242 of the flow-rate regulator 240, a flow-rate regulator separation unit 140 having a function capable of locking the flow-rate regulator 240 mounted to the dial mounting unit 130, and a controller 170.

In this case, the dial mounting unit 130 and the flow-rate regulator separation unit 140 may be configured such that when the dial 242 is mounted to the dial mounting unit 130, the dial 242 passes through the flow-rate regulator separation unit 140 and is then mounted to the dial mounting unit 130.

In another embodiment of the present invention, the flow-rate regulator separation unit 140 may include a locking means for preventing arbitrary separation of the flow-rate regulator 240 mounted to the dial mounting unit 130, an unlocking means for separating the flow-rate regulator 240 from the dial mounting unit 130, and a separation means for applying a force in a direction in which the flow-rate regulator 240 is separated from the dial mounting unit 130 by the operation of the unlocking means.

The flow-rate regulator separation unit 140 may include a hollow flow-rate regulator separation unit body 141 provided to be rotatable, and support grooves 145 formed in respective upper and lower portions of the flow-rate regulator separation unit body 141, the locking means may include a locking bar 142 formed in the front of each of the support grooves 145, the unlocking means may include an unlocking protrusion 146 protruding from one side of the flow-rate regulator separation unit body 141, and the separation means may include a separation slope 144 formed at one side within each of the support grooves 145.

The unlocking protrusion 146 may include a button 146d formed with a stopper 146e capable of preventing the flow-rate regulator separation unit body 141 from being arbitrarily unlocked.

In a still another embodiment of the present invention, the main body 110 may be further provided with an input unit 150 and an output unit 160, and the controller 170 may be configured to derive a target rotational position of the dial 242, corresponding to an input target flow rate $Q_t$, from an equation of $Q=C \cdot H$ representing a relationship between a flow rate Q, a level difference H, and an overall flow coefficient C varied with the rotation of the dial 242 of the flow-rate regulator 240.

In the still another embodiment of the present invention, the controller 170 may be configured to measure an actual flow rate $Q_m$ at normal times or at every preset period to display it on the output unit 160 and to readjust the target rotational position of the dial 242 by means of a correlation between the rotational position of the dial 242, the actual flow rate $Q_m$, and the target flow rate $Q_t$ when acceleration of a drip chamber 210 of an infusion solution set 200 connected to the flow-rate regulator 240 is less than or equal to a preset threshold and a difference $\Delta Q$ between the measured actual flow rate $Q_m$ and the target flow rate $Q_t$ is greater than a preset value.

In the still another embodiment of the present invention, when acceleration of a drip chamber 210 of an infusion solution set 200 connected to the flow-rate regulator 240 exceeds a preset threshold, the controller 170 may be configured such that a drop falling within a preset time t in excess of the acceleration threshold is not used to calculate an actual flow rate $Q_m$, thereby maintaining a previous flow rate $Q_m$ to be displayed on the output unit 160, whereas a drop falling after elapse of the preset time t in excess of the acceleration threshold is used to calculate the actual flow rate $Q_m$.

When the number of drops, the drops not being used for detection of the actual flow rate $Q_m$, exceeds a preset number in unit time, the controller 170 may be configured to inform of it through a warning sound and/or a warning light and/or a warning message.

In a still yet another embodiment of the present invention, the controller 170 may be configured to derive a time interval of falling infusion solution drops corresponding to an input target flow rate $Q_t$, to rotate the dial 242 of the flow-rate regulator 240 at every time interval until one drop falls, and to rotate the dial 242 in reverse after the drop falls.

In a further embodiment of the present invention, the controller 170 may be configured to measure an infusion solution drop rate and calculate an actual flow rate $Q_m$ by multiplying the drop rate by a drop volume.

The controller 170 may be configured to store volume change data of drop according to an infusion solution drop rate and/or a temperature of the infusion solution and to correct an actual flow rate $Q_m$ at the time of calculation of the actual flow rate $Q_m$.

The controller 170 may be configured to store a relationship between changes in drop volume to a gradient of a drip chamber 210 of an infusion solution set 200 connected to the flow-rate regulator 240 as data and to correct an actual flow rate $Q_m$ by reflecting the data at the time of calculation of the actual flow rate $Q_m$ when acceleration of the drip chamber between falling drops does not exceed a threshold and the gradient is maintained within a preset difference $\Delta \theta$ at a specific value.

Advantageous Effects of Invention

The infusion flow-rate regulating device of the present invention having the above configuration can automatically control a flow rate of the infusion by a target flow rate input thereto.

In addition, it is possible to safely and rapidly perform injection of an infusion solution to a patient at a target flow rate by the method of deriving a target rotational position corresponding to the target flow rate through information on the flow rate measured once at an arbitrary initial rotational position.

Moreover, the infusion flow-rate regulating device of the present invention can stably perform injection of an infusion solution by rapidly adjusting the flow rate to a target flow rate through single flow rate control even though the setting of the infusion solution set is changed while monitoring the flow rate during injection of an infusion solution according to the target flow rate.

Furthermore, the infusion flow-rate regulating device of the present invention can safely and accurately perform injection of an infusion solution to a patient at a target flow rate by the method of supplying a drop by rotating the dial of the flow-rate regulator mounted thereto at every time interval of falling drops corresponding to the target flow rate. Thought such a configuration, it is possible to effectively and safely supply a fluid at the target flow rate, particularly, even when the drop interval (or period) is long as the target flow rate is small.

Finally, the infusion flow-rate regulating device of the present invention can be easily used in the clinical site by allowing easy attachment and detachment of the flow-rate regulator and having a conveniently portable size since the dial mounting unit for mounting and rotating the flow-rate regulator and the flow-rate regulator separation unit have a simple and compact structure.

The present invention is not limited to the above effects, and it should be understood that the present invention includes all effects which can be inferred from the following detailed description of the present invention or the configuration of the invention defined by the appended claims.

BRIEF DESCRIPTION OF DRAWINGS

FIG. 8A and FIG. 8B are an assembled view illustrating the infusion flow-rate regulating device 100 according to the first embodiment of the present invention, wherein FIG. 8A is an assembled view illustrating the infusion flow-rate regulating device and FIG. 8B is an assembled view illustrating the infusion flow-rate regulating device equipped with a flow-rate regulator.

FIG. 9A and FIG. 9B are an exploded view illustrating an infusion flow-rate regulating device 100 according to a second embodiment of the present invention, wherein FIG. 9A is a first perspective view illustrating the infusion flow-rate regulating device and FIG. 9B is a second perspective view illustrating the infusion flow-rate regulating device.

FIG. 10A and FIG. 10B are an assembled view illustrating the infusion flow-rate regulating device 100 according to the second embodiment of the present invention, wherein FIG. 10A is an assembled view illustrating the infusion flow-rate regulating device and FIG. 10B is an assembled view illustrating the infusion flow-rate regulating device equipped with a flow-rate regulator.

FIG. 12A and FIG. 12B are graphs illustrating a change in flow rate with the rotational position of a dial in the flow-rate regulator, wherein FIG. 12A is a graph illustrating a change in flow rate and a change in overall flow coefficient C to the angle of rotation and FIG. 12B is a graph illustrating a change in flow rate to the gradation flow rate.

DESCRIPTION OF EMBODIMENTS

Figure 1:
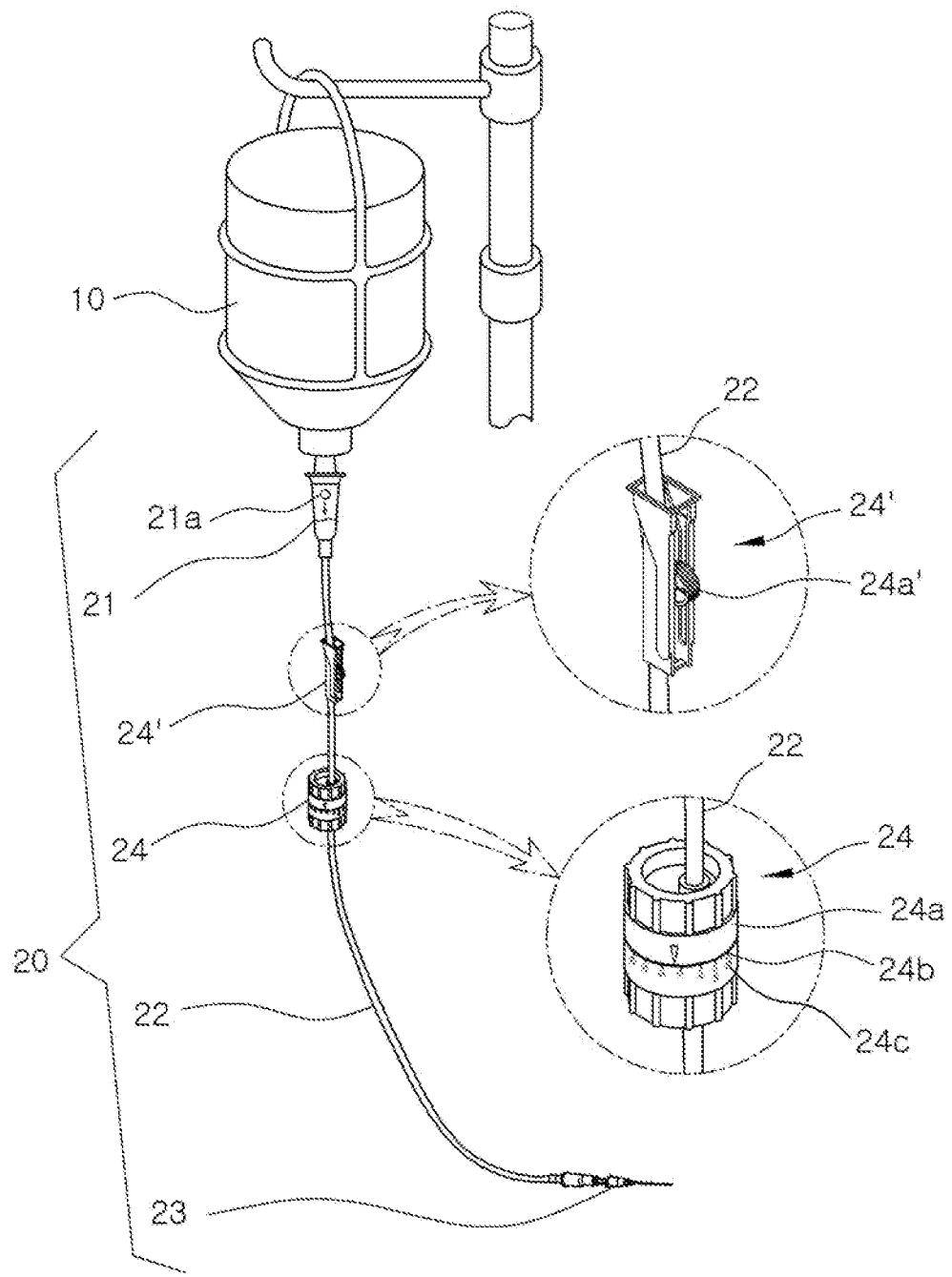
FIG. 1 is a view illustrating a state of a typical infusion solution set.
Figure 2:
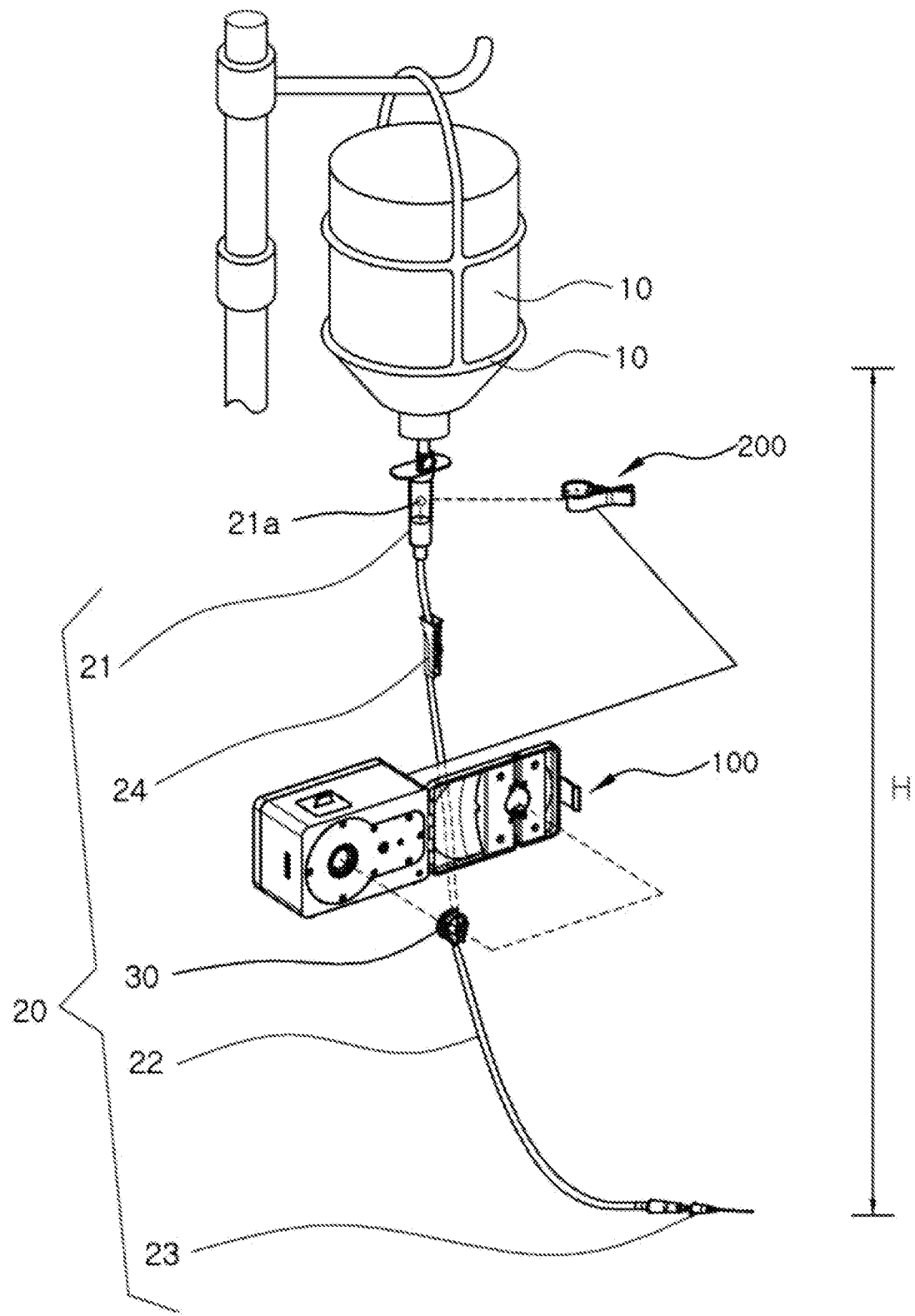
FIG. 2 is a view illustrating a state of a conventional infusion flow-rate regulating device and infusion solution set.

Reference will now be made in detail to exemplary embodiments of the present invention, examples of which are illustrated in the accompanying drawings. The present invention may, however, be embodied in different forms and should not be construed as limited to the embodiments set forth herein. For clear explanation of the present invention, parts irrelevant to the description may be omitted in the drawings, and like reference numerals refer to like parts throughout the specification.

In the whole specification, it will be understood that when an element is referred to as being "connected (led, contacted, or coupled)" to another element, it can be "directly connected" to the other element or it can be "indirectly connected" to the other element with other elements being interposed therebetween. In addition, it will be understood that when a component is referred to as being "comprising or including" any component, it does not exclude other components, but can further comprise or include the other components unless otherwise specified.

Hereinafter, preferred embodiments of the present invention will be described in detail with reference to the accompanying drawings so as to be easily embodied by those skilled in the art to which the present invention pertains.

Figure 3:
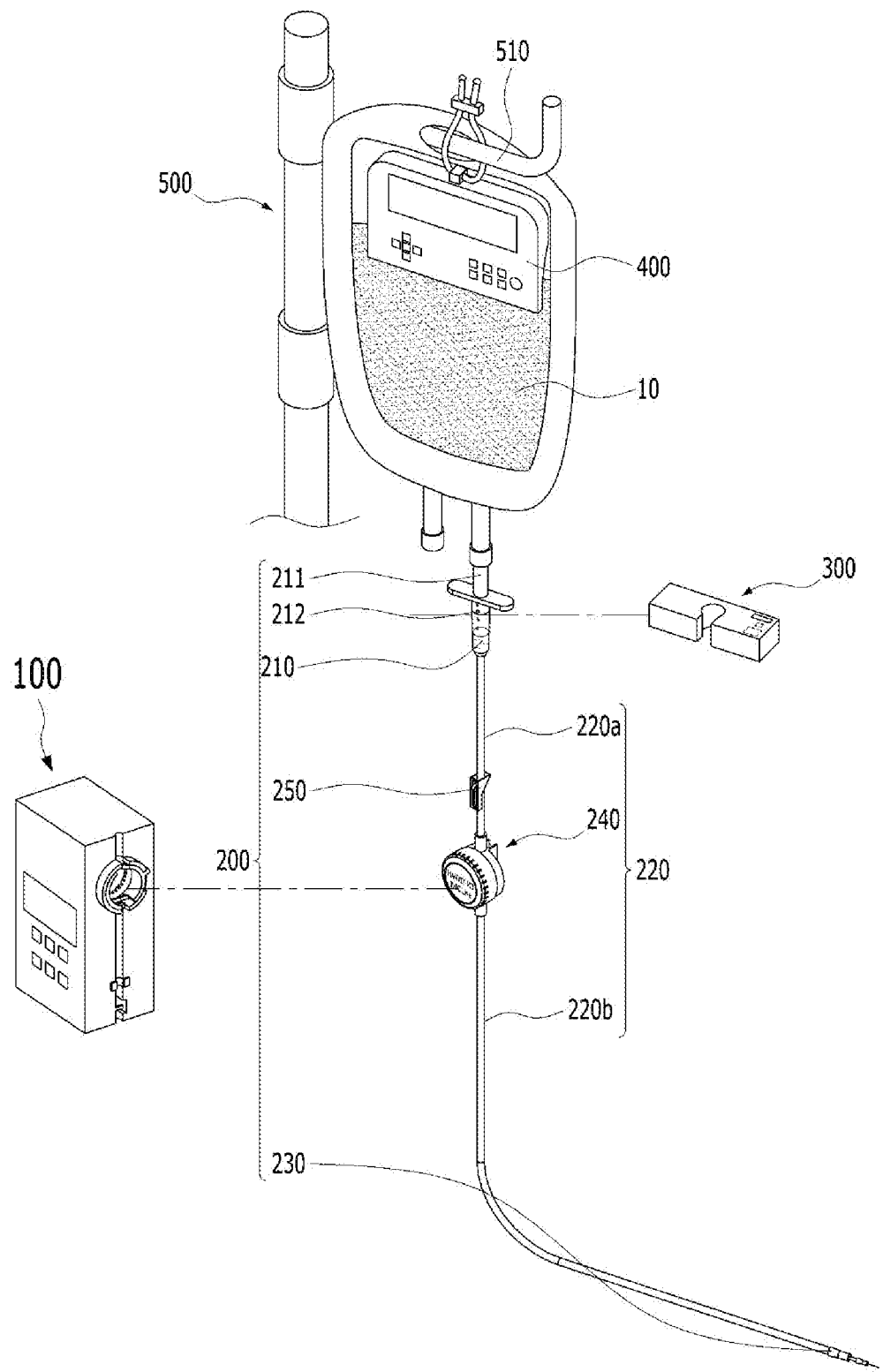
FIG. 3 is a view illustrating a state of an infusion flow-rate regulating device and an infusion solution set according to the present invention.

FIG. 3 is a view illustrating a configuration of an infusion flow-rate regulating device 100 according to an embodiment of the present invention used in an infusion solution set 200 together with a drop sensor 300.

Figure 4:
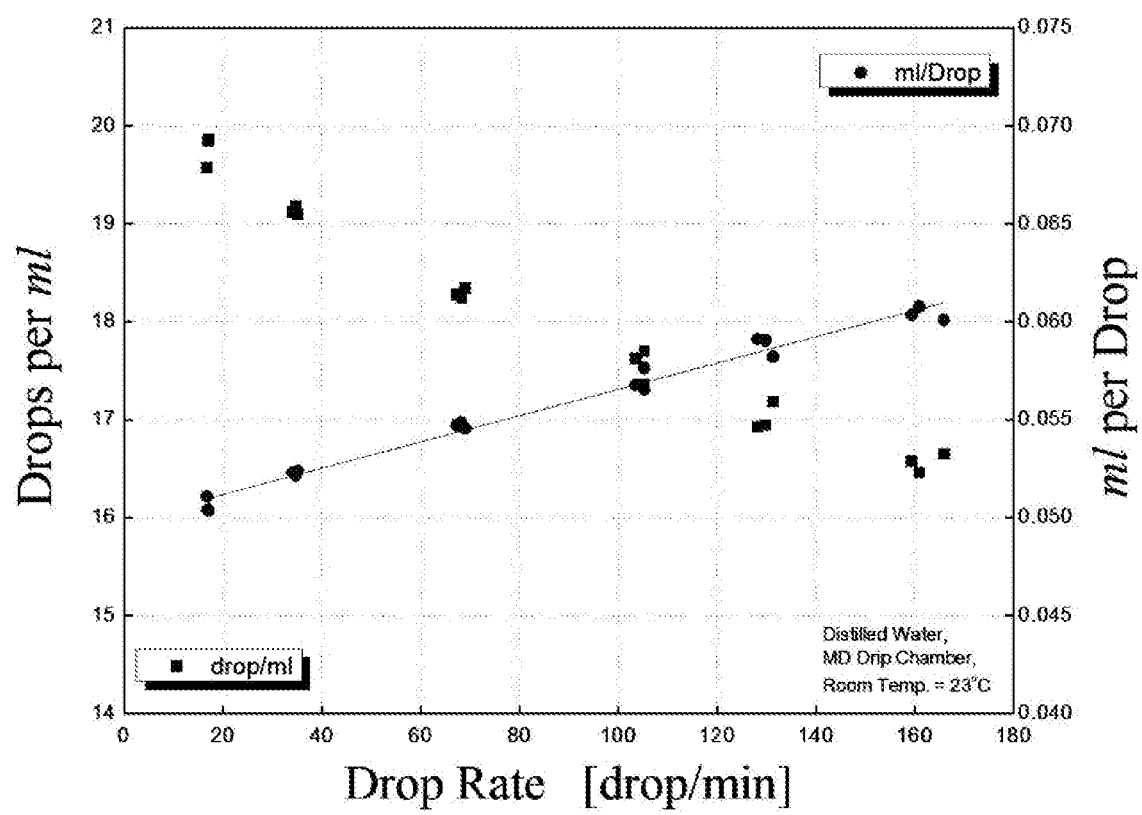
FIG. 4 is a graph illustrating a relationship between a drop rate and a drop volume.

Prior to description of the infusion flow-rate regulating device 100 and the drop sensor 300, the infusion solution set 200 will be described in brief with reference to FIGS. 3 to 5.

First, the volume of an infusion solution drop 212 falling in a drip chamber 210 included in the infusion solution set 200 may slightly vary with the drop rate, the gradient of the drip chamber, the temperature of the infusion solution, and the like. By way of example, it can be seen that the volume of the drop increases as the rate of the drop 212 increases up to a certain rate, as illustrated in FIG. 4. The volume of the drop may be affected by the gradient of the drip chamber 210, the change in temperature of the infusion solution, or the like.

In the measurement of a flow rate, the flow rate may be calculated by simply multiplying a drop volume by a drop rate in the state in which the drop volume is regarded as a constant value regardless of the change in the drop rate. However, the flow rate may be more accurately measured by reflecting a change in the drop volume to the drop rate. This may be easily implemented in such a manner that the change in the drop volume to the drop rate, which is experimentally obtained as in a graph illustrated in FIG. 4, is previously stored as data in a controller 170 of the infusion flow-rate regulating device 100 which will be described later. In addition, the correlation between the gradient of the drip chamber, the temperature of the infusion solution, or the like and the drop volume may be experimentally established as data, and this correlation may be previously stored in the controller 170 of the infusion flow-rate regulating device 100 for the reflection thereof as occasion demands.

The meaning, "stored as data in the controller 170", in the present invention also includes a state in which a plurality types of data is created and stored as a function by interpolation, curve fitting, or the like to check corresponding values to all points of respective parameters. Since manufacturers may have different types of characteristic information on the drip chamber 210, the data may be sorted for each manufacturer and stored to be selectable. In addition, the information on the drop volume may be sorted and stored for each type of the drip chamber 210 for use. For example, it is possible to sort and store information on the drop volume for an adult drip chamber of 20 drops per cc and for an infant/child drip chamber of 60 drops per cc.

Next, a flow-rate regulator 240 used in the embodiment of the present invention will be described. As illustrated in FIG. 5, the flow-rate regulator 240 includes upper and lower tube connections 241a and 241b disposed at the respective upper and lower portions thereof, and a body 241 having a handle 241c disposed at the rear surface thereof. In addition, the flow-rate regulator 240 includes an internal passage (not shown) formed therein and a dial 242 that is rotatably mounted to the body 241 to vary the internal passage depending on the adjustment of a rotational position.

The dial 242 has an irregularity 242c formed around the outer peripheral surface thereof to prevent slip when the dial 242 is gripped by a hand or mounted to a dial mounting unit 130 to be described later. The dial 242 may have an initialization calibration or groove or protrusion 242d formed on the bottom or circumferential surface thereof to indicate a position for blockage of injection (or minimum flow rate). Meanwhile, the body 241 may also have a reference protrusion or calibration 241d formed to be aligned with the initial position of the initialization calibration or protrusion 242d.

Figure 5:
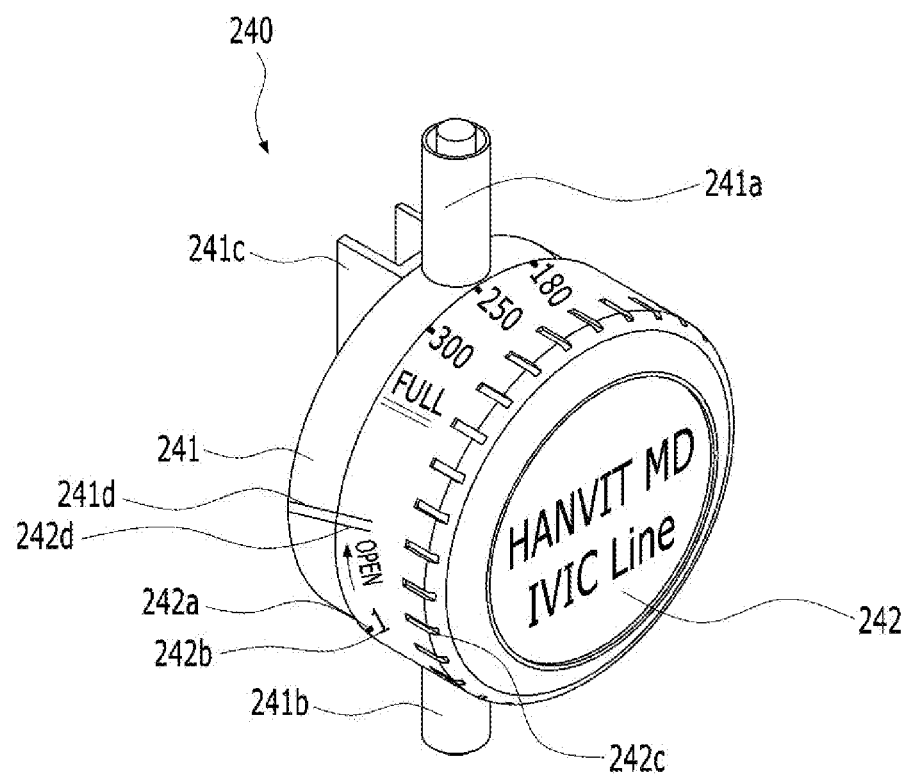
FIG. 5 is a perspective view illustrating a flow-rate regulator used for the present invention.

As illustrated in FIG. 5, the dial 242 of the flow-rate regulator 240 has a calibration 242a and a corresponding number 242b that visually indicate the rotational position thereof. The calibration 242a and the number 242b may indicate the angle of the dial 242 and the figure corresponding thereto, or may also be indicated as a gradation flow rate 242b as the flow rate $Q_m$ experimentally measured by rotating the dial 242 under the conditions of a specific level difference H and a specific temperature.

Next, the drop sensor 300 mounted to the drip chamber 210 of the infusion solution set will be described with reference to FIG. 6.

Figure 6:
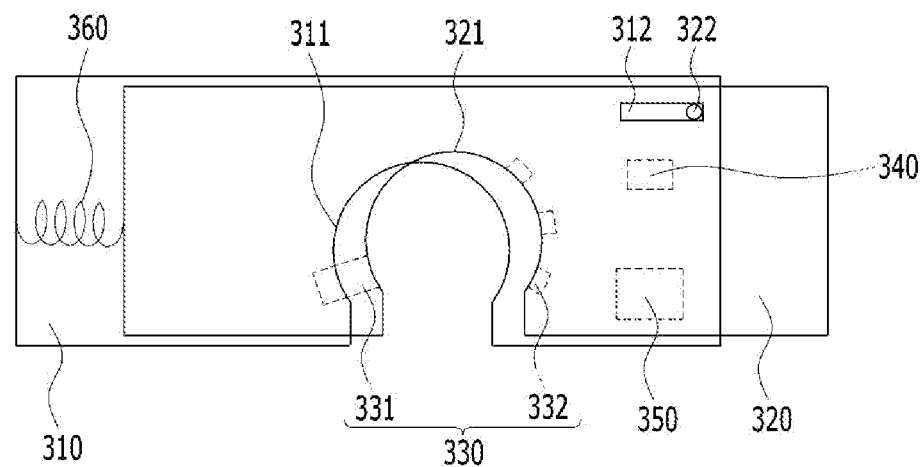
FIG. 6 is a cross-sectional view illustrating a drop sensor 300 used in an infusion solution set.

FIG. 6 illustrates an example of the drop sensor 300 with a C or U shape, which may be detachably attached to the side of the drip chamber 210.

The drop sensor 300 includes a drop sensing part 330 for detecting whether a drop falls and a motion sensing part 340 for detecting movement of an infusion solution bag 10 or the drip chamber 210.

In an embodiment of the drop sensing part 330 illustrated in FIG. 6, the drop sensing part 330 consists of a light emitting element 331 and a light receiving element 332 that face each other on an inner surface surrounding the drip chamber 210 in a second groove 321 of a second body 320 to detect whether a drop falls. The light receiving element 332 receives light emitted from the light emitting element 331 to pass through the drip chamber 210. Various types of known light such as infrared rays and laser beams may be used as the light from the light emitting element 331.

An embodiment of the motion sensing part 340 illustrated in FIG. 6 is formed at the second body 320 to detect the movement of the infusion solution bag 10 or the drip chamber 210. The motion sensing part 340 consists of a three-axis accelerometer or a three-axis accelerometer and a gyro sensor to measure a three-axis acceleration, an angular acceleration, a gradient, etc.

The drop sensor 300 may include a separate calculation part 350 to calculate a measurement value through the signals detected by the drop sensing part 330 and the motion sensing part 340, and the controller 170 provided in the infusion flow-rate regulating device 100, which will be described later, may integrally perform calculation and control.

In addition, necessary information such as information measured or calculated in the drop sensor 300 may be displayed on an output unit 160 formed in the infusion flow-rate regulating device 100, which will be described later.

Next, an infusion flow-rate regulating device 100 according to a first embodiment of the present invention will be described with reference to FIGS. 3 and 7.

Figure 7:
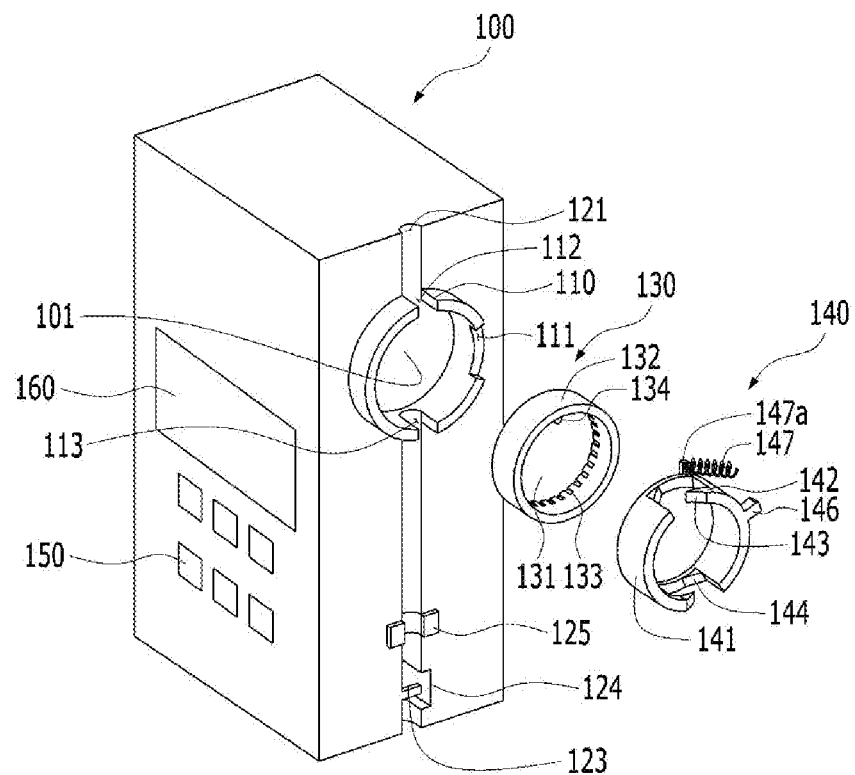
FIG. 7 is an exploded view illustrating an infusion flow-rate regulating device 100 according to a first embodiment of the present invention.

In the first embodiment, the infusion flow-rate regulating device 100 includes a main body 110 and a dial mounting unit 130, as illustrated in FIGS. 3 and 7. The main body 110 may include an input unit 150 for input of data and an output unit 160 for display of information such as a flow rate, which are formed at one side thereof. The main body 110 is provided therein with a controller 170 and a drive motor (not shown) connected to the dial mounting unit 130 to adjust an angle of rotation and a direction.

As illustrated in FIG. 7, the dial mounting unit 130 is formed at one side of the main body 110. In FIG. 7, the dial mounting unit 130 is mounted in a dial mounting unit installation part 111 formed at one side of the main body 110 for coupling with the drive motor (not shown). The dial mounting unit 130 may protrude according to the shape of the main body 110, but will be described about the configuration illustrated in FIG. 7 in the present embodiment. As illustrated in FIG. 7, an upper mounting portion 121 is formed at the upper portion of the dial mounting unit installation part 111 of the main body 110. The upper mounting portion 121 is configured to detachably attach the upper portion of the flow-rate regulator 240, namely the upper tube connection 241a. The dial mounting unit installation part 111 has an intermediate mounting portion 122 formed at the lower portion thereof. The intermediate mounting portion 122 is configured to detachably attach the lower portion of the flow-rate regulator 240, namely the lower tube connection 241b. In addition, the intermediate mounting portion 122 may be elongated, as illustrated in FIG. 7, for installation of the lower tube 220b. A lower mounting portion 124 is formed beneath the intermediate mounting portion 122 to detachably attach the lower tube 220b. A bubble sensor 125 may be installed between the intermediate mounting portion 122 and the lower mounting portion 124. In addition, the lower mounting portion 124 may be further formed with a fixed protrusion 123 to prevent the separation of the lower tube 220b from the main body 110.

The dial mounting unit 130 has a structure capable of rotating the dial 242 by easy mounting of the flow-rate regulator 240, and the structure thereof will be described in detail with reference to FIG. 7. The dial mounting unit 130 has a mounting unit bottom 131 coupled to the drive motor (not shown) and a mounting unit side 132 protruding forward along the edge of the bottom 131 for insertion and gripping of the dial 242. In addition, the mounting unit side 132 may have a side irregularity 133 formed on the inner surface thereof such that the side irregularity 133 is engaged to the irregularity 242c formed on the dial 242 for more stable coupling with the dial 242 of the inserted flow-rate regulator 240. In addition, the mounting unit bottom 131 may be formed with a bottom irregularity 134 as occasion demands for coupling and/or positioning with the dial 242. Meanwhile, the mounting unit side 132 may have a reference line (not shown) formed on the outer surface thereof to indicate a reference position.

When the flow-rate regulator 240 is mounted to the dial mounting unit 130, the controller 170 to be described later preferably controls the side irregularity 133, the bottom irregularity 134, or the reference line (not shown) to be aligned at an initial alignment position.

In order to use the infusion flow-rate regulating device 100 with safety in the clinical site in the present invention, as illustrated in FIG. 7, the infusion flow-rate regulating device 100 further includes a flow-rate regulator separation unit 140 that may prevent the separation of the upper and lower portions of the flow-rate regulator 240 from the state in which they are coupled to the upper and intermediate mounting portions 121 and 122, and may separate the flow-rate regulator 240 from the main body 110 with less effort if necessary.

The flow-rate regulator separation unit 140 illustrated in FIG. 7 has a hollow flow-rate regulator separation unit body 141 that is rotatable. In the present embodiment, the body 141 has an unlocking protrusion 146 as an unlocking means formed at one side thereof, and an elastic body 147 formed at the other side thereof for enabling the flow-rate regulator separation unit body 141 to be restored to its original position after rotation. The elastic body 147 may be configured such that one end thereof is coupled to an elastic body support 147a formed at the flow-rate regulator separation unit body 141 and the other end thereof is coupled to an elastic body support (not shown) formed at one side in the main body to have an elastic restoring force. Although the elastic body 147 is illustrated as being a compression coil spring in FIG. 7, other elastic bodies such as a torsion spring may be used according to the coupling structure.

In the flow-rate regulator separation unit 140 illustrated in FIG. 7, the flow-rate regulator separation unit body 141 has support grooves 145 formed in the respective upper and lower portions thereof such that the upper and lower tube connections 241a and 241b of the flow-rate regulator 240 are seated in the support grooves 145. Locking bars 142 as a locking means are formed in the front of the grooves 145 to prevent the separation of the upper and lower portions of the flow-rate regulator 240 from the main body 110. As illustrated in FIG. 7, the locking bars 142 provided in the upper and lower support grooves 145 are installed at opposite positions for the separation of the flow-rate regulator 240 when rotating the flow-rate regulator separation unit 140.

Preferably, the locking bars 142 have support slopes 143 formed at the ends thereof for easy insertion of the upper and lower tube connections 241a and 241b of the flow-rate regulator 240 when the flow-rate regulator 240 is inserted into and coupled to the main body.

Preferably, the flow-rate regulator separation unit 140 has a separation means for applying a force in the direction in which the upper and lower tube connections 241a and 241b of the flow-rate regulator 240 are separated from the upper and intermediate mounting portions 121 and 122 when the flow-rate regulator 240 is to be separated from the main body 110. In the present invention, as an example of the separation means, a separation slope 144 is formed at one side of each of the upper and lower support grooves 145, as illustrated in FIG. 7. In this case, the separation slope 144 is most preferably installed at the lower portion of the surface facing the associated locking bar 142 in each of the support grooves 145.

As illustrated in FIGS. 7 and 8, the rotating flow-rate regulator separation unit 140 is installed forward of the dial mounting unit 130 after the dial mounting unit 130 is installed in the dial mounting unit installation part 111 of the main body 110. Accordingly, it is possible to implement a convenient and compact infusion flow-rate regulating device through the structure in which the flow-rate regulator separation unit 140 has a rotary shaft in the same direction as the dial mounting unit 130 in the front thereof.

For safe operation of the flow-rate regulator separation unit 140, a flow-rate regulator separation unit guide 112 is preferably formed around the installation part 111 of the main body 110, as illustrated in FIGS. 7 and 8. The flow-rate regulator separation unit guide 112 has an unlocking protrusion guide 113 formed at one side thereof for the operation of the unlocking protrusion 146. In addition, the flow-rate regulator separation unit guide 112 has upper and lower guides 114 and 115 formed at the upper and lower portions thereof such that the upper and lower tube connections 241a and 241b of the flow-rate regulator 240 may move to be mounted to or separated from the support grooves 145 of the flow-rate regulator separation unit 140 and the upper and intermediate mounting portions 121 and 122 of the main body 110.

Figure 8A:
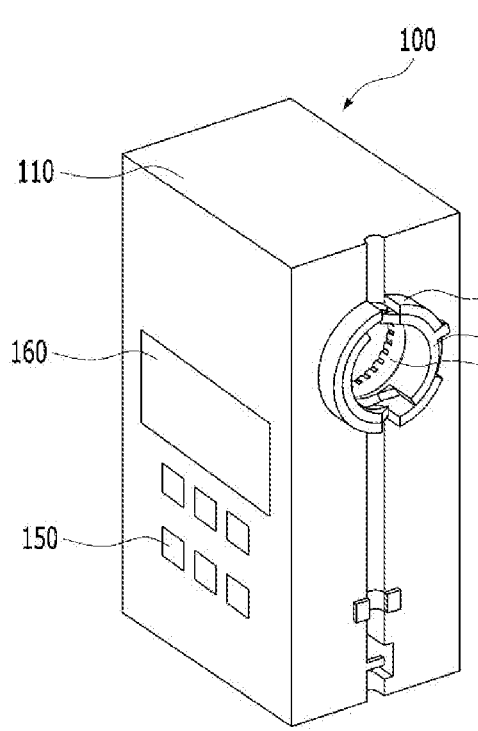
Figure 8B:
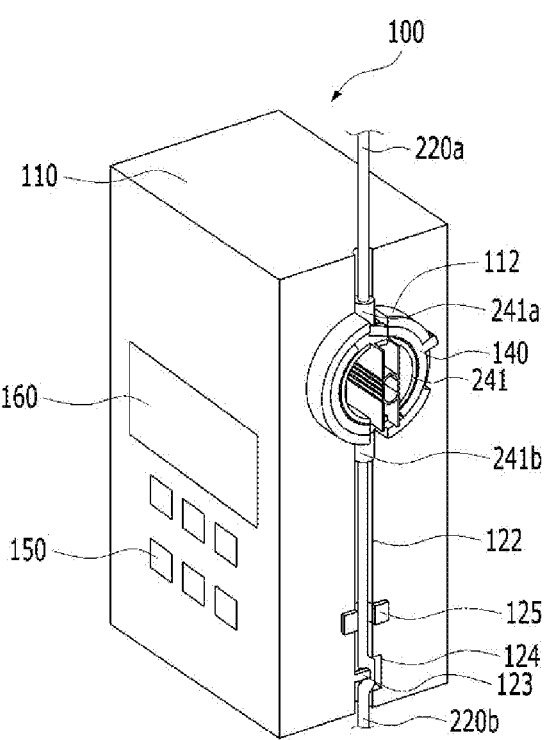

FIG. 8A illustrates the infusion flow-rate regulating device 100 of the first embodiment, and FIG. 8B illustrates the infusion flow-rate regulating device 100 equipped with the flow-rate regulator 240.

The dial 242 of the flow-rate regulator 240 is coupled to be directed toward the dial mounting unit 130 by gripping the handle 241c formed in the body 241 of the flow-rate regulator 240 after the dial 242 is placed at an initial position for blockage of injection (or minimum flow rate) and the dial mounting unit 130 is aligned at an initial position. Thus, the upper and lower tube connections 241a and 241b of the flow-rate regulator 240 pass through the upper and lower guides 114 and 115 of the main body 110 to meet with the support slopes 143 of the locking bars 142 of the flow-rate regulator separation unit 140. In this case, the flow-rate regulator separation unit 140 is rotated clockwise (description of the configuration illustrated in FIG. 8) by the movement of the support slopes 143 when a force is continuously applied thereto, and thus the locking bars 142 rotate so that the upper and lower tube connections 241a and 241b of the flow-rate regulator 240 are seated in the support grooves 145 and fixed to the upper and intermediate mounting portions 121 and 122. In addition, the dial 242 of the flow-rate regulator 240 is coupled to the dial mounting unit 130 installed behind the flow-rate regulator separation unit 140. Since the locking bars 142 are restored to their original positions by restoring force, the upper and lower tube connections 241a and 241b of the flow-rate regulator 240 are locked by the locking bars 142 as a locking means while being fixed to the upper and intermediate mounting portions 121 and 122 so as not to be separated from the main body 110 without the operation of the unlocking protrusion 146.

When the unlocking protrusion 146 as an unlocking means is rotated clockwise for the separation of the flow-rate regulator 240, the locking bars 142 are rotated in the direction in which the locking of the upper and lower tube connections 241a and 241b of the flow-rate regulator 240 is released, and the opposite separation slopes 144 apply a force in the direction in which the upper and lower tube connections 241a and 241b of the flow-rate regulator 240 are separated from the upper and intermediate mounting portions 121 and 122. Therefore, it is possible to easily separate the flow-rate regulator 240 from the main body 110.

FIGS. 9 and 10 illustrate an infusion flow-rate regulating device 100 according to a second embodiment of the present invention. This has the same configuration as that in the first embodiment illustrated in FIGS. 7 and 8 in most cases, but differs from that in the first embodiment in terms of some configuration.

As illustrated in FIGS. 9 and 10, an unlocking protrusion 146 at one side of a flow-rate regulator separation unit 140 in the second embodiment includes a body 146a and a button 146d to be moved relative to the body 146a.

Figures 10A, 10B:
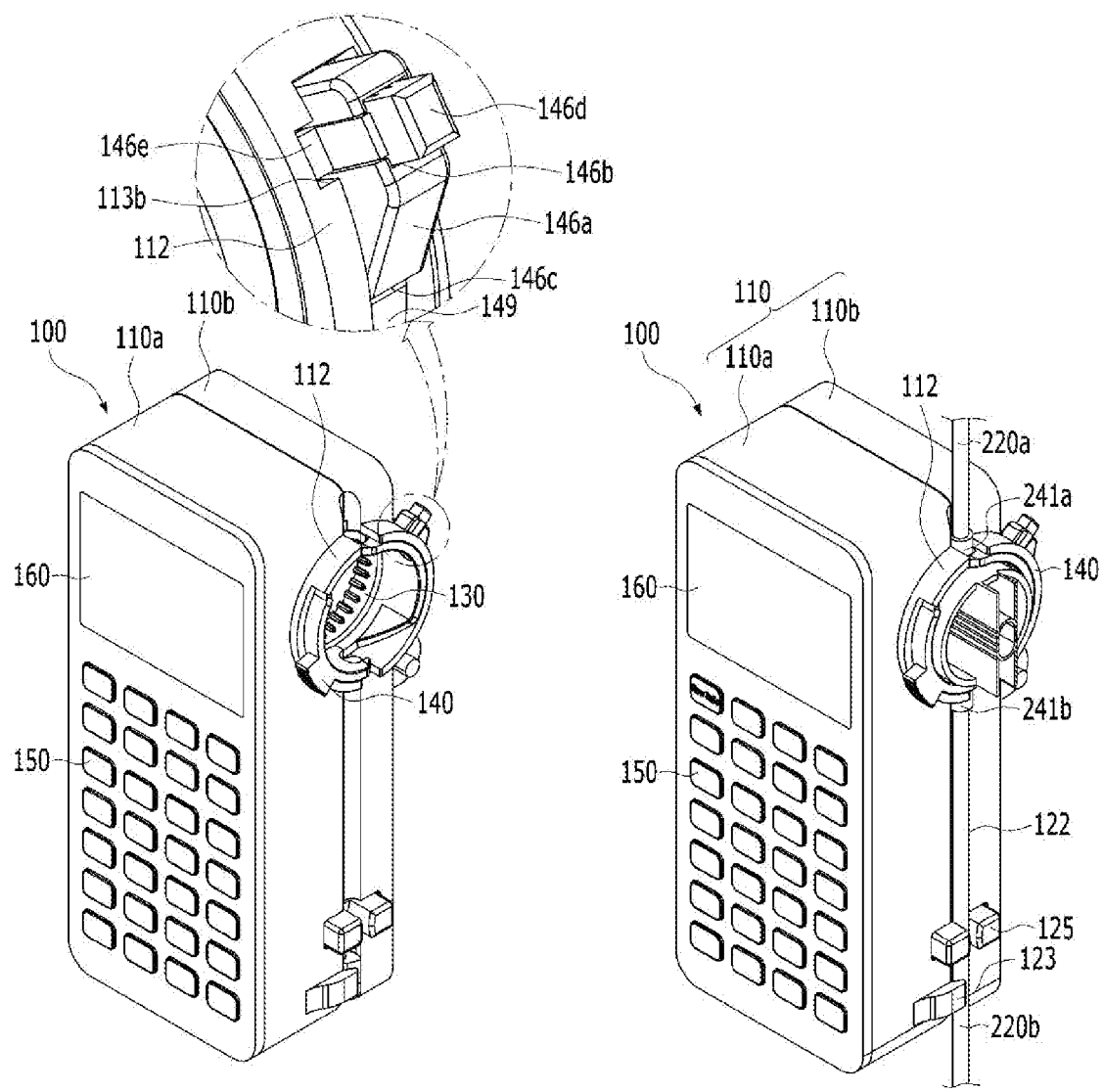

As illustrated in FIG. 10A, the unlocking protrusion 146 in the second embodiment includes a body 146a formed to be in contact with the flow-rate regulator separation unit body 141 and a flange 146c formed on the bottom of the body 146a. In addition, the body 146a is formed with a button installation portion 146b in which the button 146d is movably installed. The button 146d has a stopper 146e protruding from one side thereof, and the stopper 146e moves along with the button 146d once the button 146d is pressed. The button 146d is preferably coupled to the body 146a through an elastic body (not shown) so as to be restored to its original position when the force pressing the button 146d is removed.

Figure 9A:
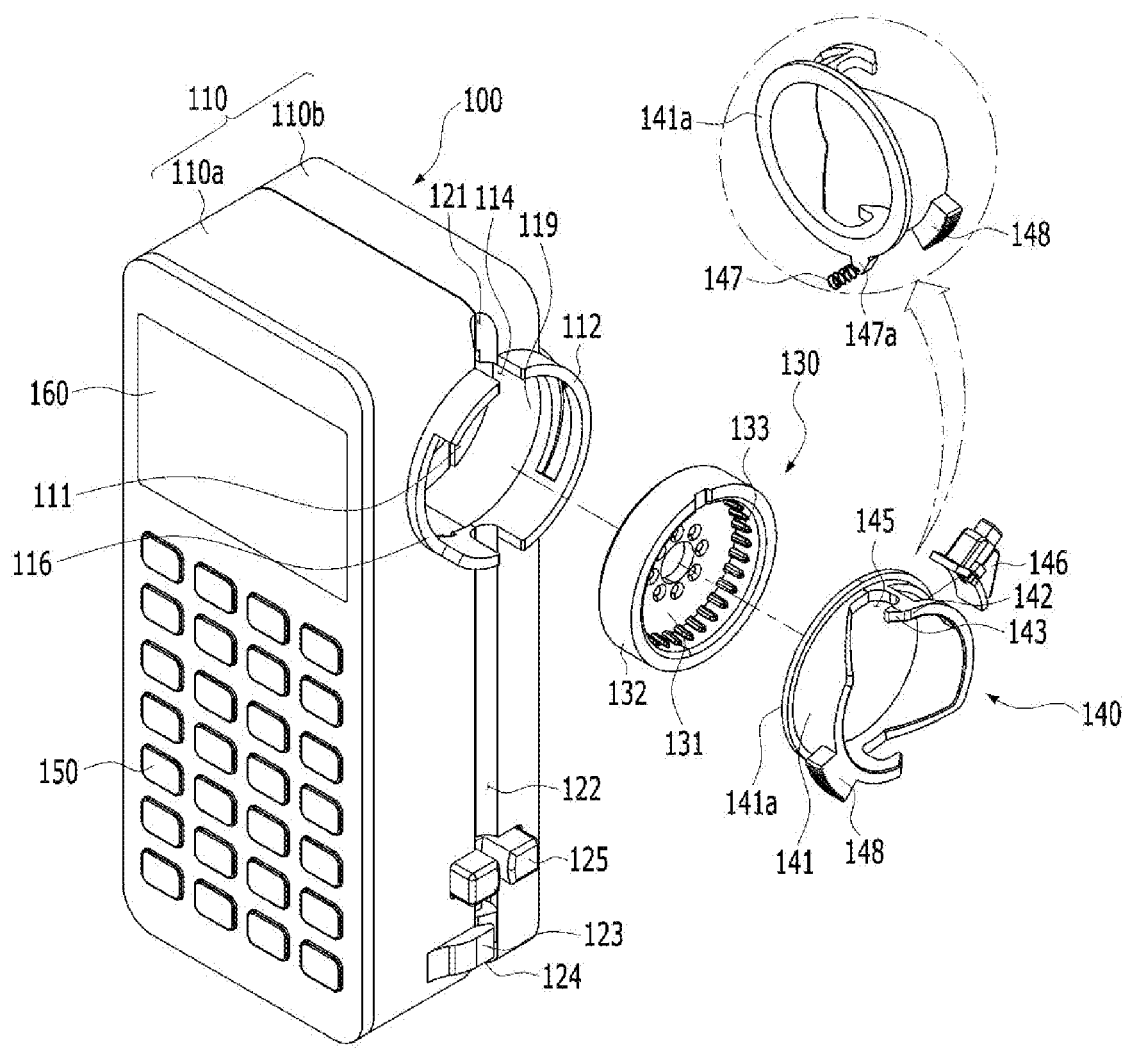
Figure 9B:
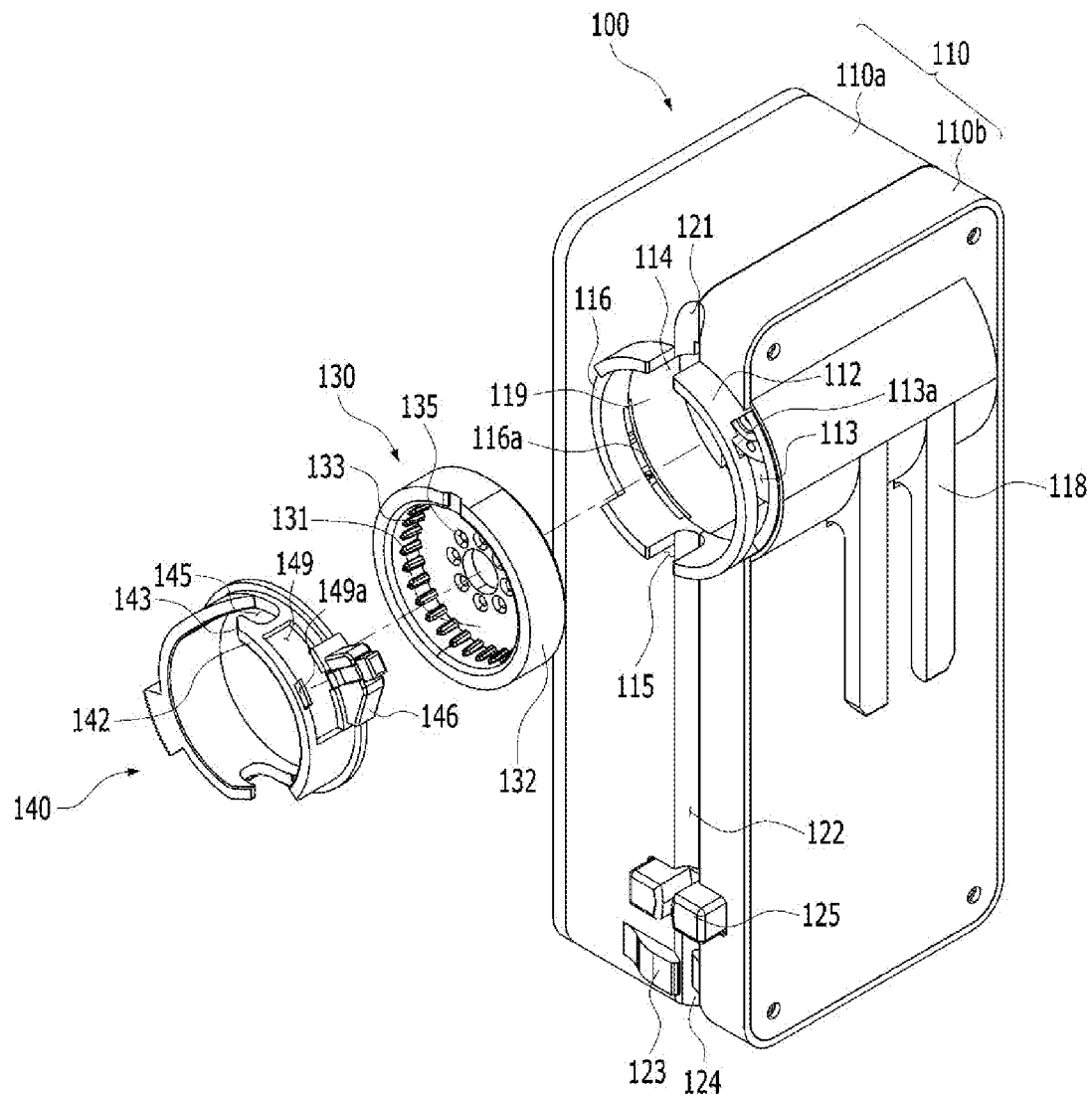

As illustrated in FIG. 9B, the flow-rate regulator separation unit body 141 may have a flange seating part 149 formed to seat the flange 146c. The flange seating part 149 may have a coupling hole 149a or a coupling groove such that the stopper 146e of the unlocking protrusion 146 is coupled to the coupling hole 149a or the coupling groove.

As illustrated in FIG. 9A, the flow-rate regulator separation unit body 141 may further have an auxiliary protrusion 148, together with the unlocking protrusion 146, for easy separation of the flow-rate regulator 240.

As illustrated in FIGS. 9 and 10, the infusion flow-rate regulating device 100 according to the second embodiment also has a flow-rate regulator separation unit guide 112 formed in the front of the main body 110. The flow-rate regulator separation unit guide 112 is provided with an unlocking protrusion guide 113, and the unlocking protrusion guide 113 further has a latch groove 113a to restrict the movement of the stopper 146e in the second embodiment. As seen in the enlarged view of FIG. 10A, the movement of the stopper 146e formed in the button 146d is restricted by the latch groove 113a at normal times. The unlocking protrusion 146 may be rotated only when the stopper 146e is separated from the latch groove 113a by pressing the button 146d.

As illustrated in FIG. 9A, the flow-rate regulator separation unit body 141 has an elastic body support 147a formed at one side of the rear thereof, and an elastic body 147 may be coupled between the elastic body support 147a and the main body 110. The elastic body 147 may be coupled in various manners. In the present invention, as illustrated in FIG. 9B, the elastic body support 147a is inserted into an elastic body guide 116a formed in the main body 110 to be coupled with the elastic body 147 in the main body 110. The elastic body 147 may be any element as long as the flow-rate regulator separation unit body 141 is restored to its original position. Although the elastic body 147 is illustrated as being a compression coil spring in FIG. 9A, other elastic bodies such as a torsion spring may be used according to the coupling structure.

Accordingly, when the elastic body 147 is coupled to the flow-rate regulator separation unit body 141, the flow-rate regulator separation unit body 141 is temporarily rotated and then restored back to its original position when the flow-rate regulator 240 is coupled to the main body. In this case, the unlocking protrusion 146 does not rotate since the stopper 146e is latched to the latch groove 113a formed in the unlocking protrusion guide 113. In the infusion flow-rate regulating device 100 according to the second embodiment, the unlocking protrusion 146 may be rotated by pressing the button 146d. When the button 146d is pressed, the stopper 146e formed in the button 146d is separated from the latch groove 113a while moving downward, and is coupled to the coupling hole 149a formed in the flow-rate regulator separation unit body 141. That is, the unlocking protrusion 146 is in the state in which it is coupled to the flow-rate regulator separation unit body 141 in the state in which the button 146d is pressed. In this state, when the unlocking protrusion 146 is rotated, the flow-rate regulator separation unit body 141 is rotated together therewith. This process is used to separate the flow-rate regulator 240 from the infusion flow-rate regulating device 100.

When the force applied to the button 146d is removed in the state in which the unlocking protrusion 146 is rotated, the flow-rate regulator separation unit body 141 and the unlocking protrusion 146 are restored to an initial position by the restoring force of the elastic body 147, so that at the initial position, the separation button 146d is restored and the stopper 146e is latched to the latch groove 113a.

That is, in the infusion flow-rate regulating device 100 illustrated in FIGS. 9 and 10, the flow-rate regulator separation unit 140 may be rotated only when the unlocking protrusion 146 is rotated in the state in which the button 146d is pressed. Therefore, it is possible to prevent arbitrary rotation of the flow-rate regulator separation unit 140 with more safety.

As illustrated in FIGS. 9 and 10, in the case where the auxiliary protrusion 148 is formed on the flow-rate regulator separation unit body 141, it is preferable that an auxiliary protrusion guide 116 is further formed at the flow-rate regulator separation unit guide 112.

As illustrated in FIG. 9A, the flow-rate regulator separation unit body 141 may have a body flange 141a formed in the rear thereof. In the case where the flange 141a is formed in the flow-rate regulator separation unit body 141 as illustrated in FIG. 9A, it is preferable that the main body 110 has a stepped portion 119 corresponding to the installation position of the flow-rate regulator separation unit 140, as illustrated in FIG. 9B, such that the flow-rate regulator separation unit 140 may be stably coupled to the main body 110. This configuration may be applied to the infusion flow-rate regulating device 100 of the first embodiment. However, the coupling structure of the main body 110 and the flow-rate regulator separation unit 140 is not limited to that illustrated in FIG. 9B, and any structure is sufficient as long as the flow-rate regulator separation unit 140 is stably coupled to the main body 110.

In a dial mounting unit 130 illustrated in FIGS. 9A and 9B, a fastening hole 135 is formed in the bottom 131 of the dial mounting unit 130. From this, it can be seen that the dial mounting unit 130 is coupled to a dial mounting unit installation part 111 by a typical fastener such as a bolt. This configuration may also be applied to the dial mounting unit 130 of the first embodiment. However, the coupling structure of the dial mounting unit 130 and the dial mounting unit installation part 111 is not limited to that illustrated in FIGS. 9A and 9B, and any structure is sufficient as long as the dial mounting unit 130 is stably coupled to the dial mounting unit installation part 111.

In the infusion flow-rate regulating device 100 illustrated in FIG. 9, the main body 110 is formed in such a manner that a first main body 110a is coupled to a second main body 110b. Through such a configuration, the dial mounting unit 130 and the flow-rate regulator separation unit 140 may be easily coupled to the main body 110. The structure of the main body 110 may also be applied to the infusion flow-rate regulating device 100 of the first embodiment.

The flow-rate regulator separation unit 140 according to the first and second embodiments of the present invention has a simple structure that is rotatable, but it may be a flow-rate regulator separation unit that includes an unlocking means or the like configured to rectilinearly move or rotate in a different direction from that in the above embodiments. In addition, the flow-rate regulator separation unit 140 may be automatically operated by driving a separate actuator.

The main body 110 of the infusion flow-rate regulating device 100 according to the present invention includes an input unit 150 provided for target flow rate selection, reset selection, correlation information selection and drip chamber characteristic information selection, which will be described later, by a user, and an output unit 160 that displays information to be recognized for the user, as illustrated in FIGS. 7 and 9.

Figure 11:
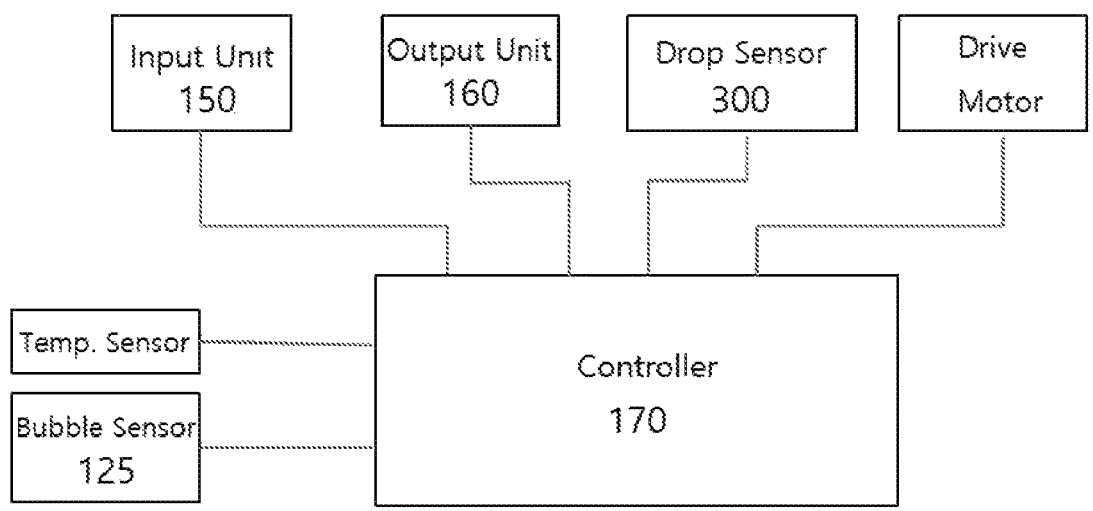
FIG. 11 is a diagram illustrating circuit connection of a controller 170.

The input unit 150 and the output unit 160 are connected to the controller 170 arranged in the device. FIG. 11 is a diagram illustrating a state in which the controller 170 is connected to other components. In this case, the connection includes wireless connection for communication as occasion demands as well as wired connection.

The controller 170 is configured for information storage, required calculation, and drive motor control, and the stored information includes correlation information between the rotational position of the dial 242 and a flow rate and characteristic information of the drip chamber 210. In addition, the information may include information about correlation between the rate, temperature, gradient, or the like of a drop and a flow rate as occasion demands.

The controller 170 is finally aimed at controlling a flow rate of the infusion to be a target flow rate $Q_t$, and the control method thereof will be described in detail below.

Firstly, the present invention uses a method of rapidly adjusting the dial 242 to a position for the target flow rate $Q_t$. To this end, since the correlation between the rotational position of the dial 242 and the flow rate Q is important, description thereof will be given in detail.

As disclosed in Korean Patent No. 10-1327862 issued to the applicant of the present invention, the correlation between the rotational position of the dial 242 and the flow rate Q may be represented by the following equation (1) since a flow of a infusion solution corresponds to a laminar flow, and the flow rate Q varies with the rotational position of the dial 242 and is proportional to each of an overall flow coefficient C, which is the coefficient determined by the length, cross-sectional area, or the like of the internal passage, and a level difference H, which is the height difference between the level of fluid contained in the infusion solution bag 10 and the injection needle 230:

$$Q = C \times H \tag{1}$$

As seen through the above equation (1), the flow rate Q has the same value as the overall flow coefficient C, which varies depending on the rotation of the dial 242 of the flow-rate regulator 240, when the level difference H is "1", and it has a value corresponding to any multiple of the overall flow coefficient C, namely a value proportional to the overall flow coefficient C even though the level difference H is not "1". Thus, the gradation flow rate 242b, which indicates that the flow rate $Q_m$ measured by rotating the dial 242 at a specific level difference H and a specific temperature is engraved on each calibration 242a of the dial 242, is proportional to the overall flow coefficient C.

Figure 12A:
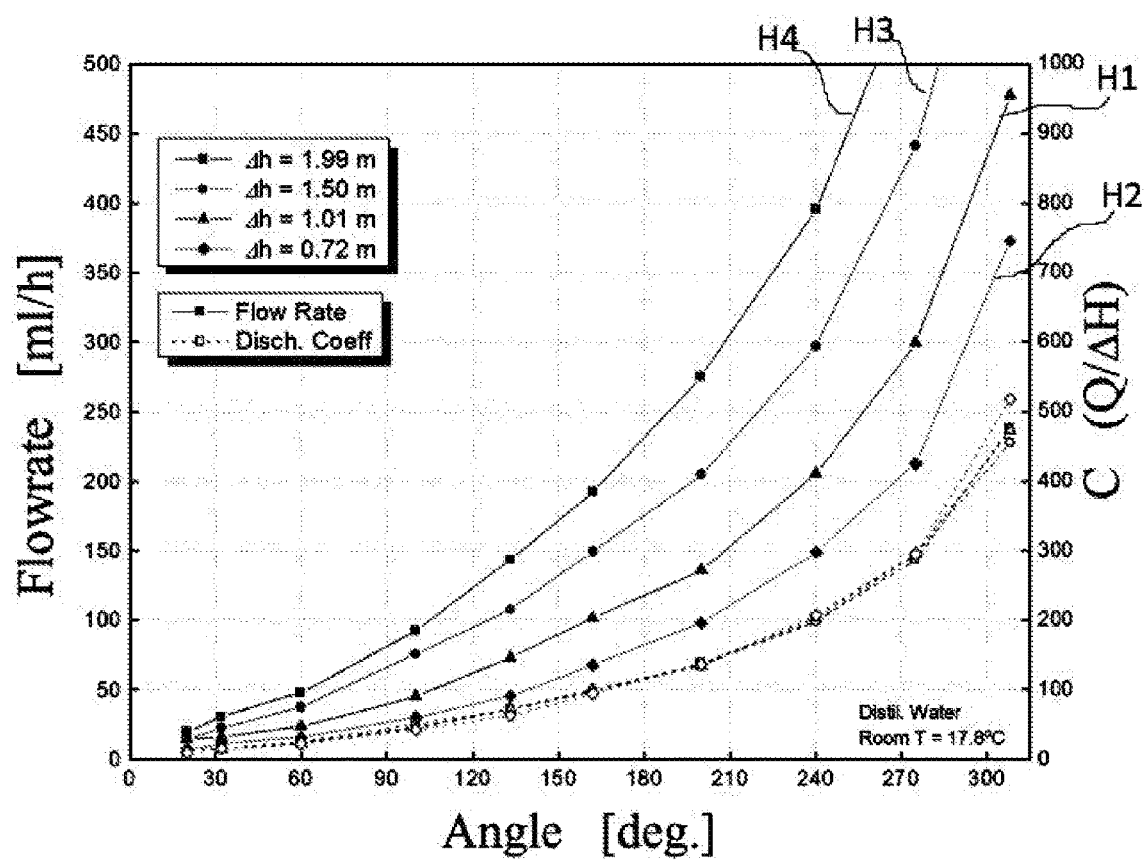
Figure 12B:
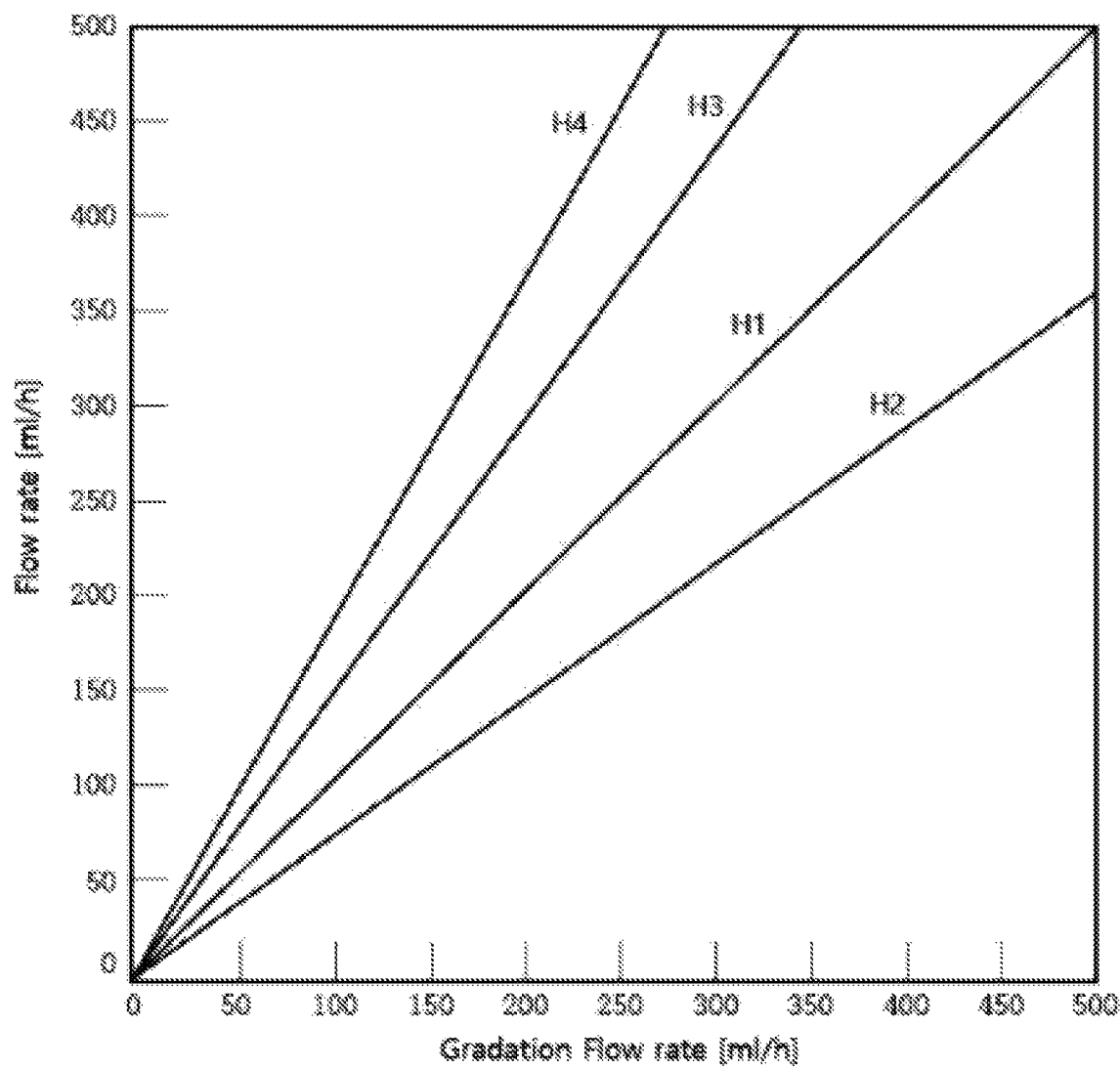

FIGS. 12A and 12B illustrate a change in flow rate to the rotation of the dial 242 in an existing flow-rate regulator 240.

FIG. 12(a) illustrates a change in flow rate Q to the angle of rotation of the dial. The relationship between the angle of rotation and the flow rate Q is not linearly changed, but it can be seen that the ratio between the flow rate Q and the level difference H at one angle of rotation is converged on one coefficient, i.e. the overall flow coefficient C, as represented in the above equation (1). In the graph relating to the overall flow coefficient C of FIG. 12A, it is possible to create data of the overall flow coefficient C through one or average of overall flow coefficients C calculated from flow rates $Q_m$ measured from different level differences H1 to H4.

FIG. 12B illustrates a change in flow rate Q to the flow rate for each angle of rotation at the specific level difference H corresponding to the above-mentioned gradation flow-rate, and illustrates that the relationship between the gradation flow-rate and the flow rate Q is linear. In the graph of FIG. 12B, it can be seen that the flow rate Q at the level difference H1 is used as a gradation flow rate.

The linear relationship between the flow rate and the gradation flow rate is not particularly recognized in the conventional flow-rate regulator. However, the inventor of the present invention found a proportional relationship between the flow rate Q and the overall flow coefficient C through the above equation (1), and found, by developing it, that the relationship between the gradation flow rate 242b and the flow rate Q is a proportional relationship while only a gradient is changed even though the level difference H is changed in the case where the gradation flow rate 242b and the overall flow coefficient C are indicated identically or in a proportional relationship in the dial 242. That is, the flow rate Q may be represented as a simple linear function, and the gradient may be represented as a simple function changed in proportion to the level difference H.

To utilize the relationship between the overall flow coefficient C or the gradation flow rate 242b and the rotational position of the dial 242, the data thereof must be previously stored in the controller 170. Experimental data of the overall flow coefficient C calculated at the specific rotational position as in FIG. 12A and/or experimental data of the gradation flow rate illustrated in FIG. 12B may each be created as a function by interpolation, curve fitting, or the like to be stored in the controller 170.

Since the overall flow coefficient C as in FIG. 12A utilizes an overall flow coefficient C according to the angle of rotation of the flow-rate regulator 240, this may be applied even when a flow-rate regulator marked with arbitrary calibration is used. FIG. 12B represented by a simple linear equation may be utilized for a flow-rate regulator marked with the gradation flow rate 242b thereof proportional to the overall flow coefficient C or when the horizontal axis is used as a value proportional to the overall flow coefficient C instead of the angle of rotation of the dial.

First, the control method of using the overall flow coefficient C will be described as follows, as illustrated in FIG. 12A.

When a target flow rate is input to the input unit 150, the controller 170 rotates the dial to an arbitrary initial rotational position. In this case, the initial rotational position may be any position allowing for a flow of the infusion solution, and the rotational position of the dial 242 corresponding to the overall flow coefficient C having the input target flow rate or the same value as the input target flow rate may also be selected as an initial rotational position. Since the values of the overall flow coefficients C at respective rotational positions are previously stored in the controller 170, a value of an overall flow coefficient $C_m$ corresponding to the initial rotational position may be obtained from the stored values. In addition, since an actual flow rate $Q_m$ may be measured from the signal of the drop sensing part 330 at the initial rotational position, an actual level difference $H_m$ is calculated from the overall flow coefficient $C_m$ and the flow rate $Q_m$ measured by means of the above equation (1). Next, since the actual level difference $H_m$ is derived, a target overall flow coefficient $C_t$ for administration at a target flow rate $Q_t$ at the actual level difference $H_m$ is derived by means of the above equation (1) again. That is, since the level difference $H_m$ is not changed, the target overall flow coefficient $C_t$ may be derived from the overall flow coefficient $C_m$ corresponding to the target flow rate $Q_t$ and the initial rotational position, and the flow rate $Q_m$ measured by means of the equation (1). Thus, it is possible to find a position corresponding to the target flow rate $Q_t$ by obtaining the angle suitable for the value of the derived overall flow coefficient $C_t$ from the stored data and rotating the dial 242 to the position suitable therefor.

Next, the control method of using data of a gradation flow rate as the flow rate Q measured for each rotational position in the state in which the level difference H between the level of fluid in the infusion solution bag 10 and the injection needle 230 is constant will be described as follows, as illustrated in FIG. 12B.

As described above, the gradation flow rate is equal to the overall flow coefficient C when the level difference H is "1", and it corresponds to any multiple of the overall flow coefficient C when the level difference H is not "1".

As illustrated in FIG. 12B, the relationship between the gradation flow rate and the flow rate after the flow rate measured for each rotational position of the dial 242 corresponds to the gradation flow rate at the position for the angle of rotation of the dial 242 in the state in which the level difference H is set as a constant value (the level difference H1 illustrated herein) may be represented by a graph passing through a coordinate (0, 0). This means that the ratio of the gradation flow rate to the flow rate has a constant value corresponding to the gradient at the specific level difference, for example an arbitrary level difference at which the infusion solution set 200 is set.

When the infusion solution set is set, namely when the level difference H is set as one value, the following equation (2) may be obtained in which the ratio between an actual flow rate $Q_m$ measured by adjusting the dial 242 to an arbitrary initial position and an initial gradation flow rate corresponding to the arbitrary initial position is equal to the ratio between a target flow rate $Q_t$ as the prescribed flow rate for intravenous (IV) treatment and a target gradation flow rate corresponding to the target flow rate:

$$\frac{\text{(target flow rate } Q_t\text{)}}{\text{(target gradation flow rate)}} = \frac{\text{(actual flow rate } Q_m\text{)}}{\text{(initial gradation flow rate)}} \quad (2)$$

In addition, the value of the target gradation flow rate may be represented by the following equation (3) by arrangement of the equation (2):

$$\text{(target gradation flow rate)} = \text{(initial gradation flow rate)} \times \frac{(Q_t)}{(Q_m)} \quad (3)$$

When a target flow rate $Q_t$ is input to the input unit 150, the controller 170 rotates the dial to an arbitrary initial rotational position corresponding to an arbitrary initial gradation flow rate. In this case, the arbitrary initial gradation flow rate may be any value, and the initial gradation flow rate may also be set to be equal to the input target flow rate $Q_t$. Since the values of the gradation flow rates at respective rotational positions are previously stored in the controller 170, a value of a rotational position corresponding to the initial gradation flow rate may be obtained from the stored values. In addition, an actual flow rate $Q_m$ may be measured from the signal of the drop sensing part 330 at the initial rotational position. In this case, since the ratio of the target flow rate $Q_t$ to the target gradation flow rate is equal to the ratio of the actual flow rate $Q_m$ to the initial gradation flow rate, the target gradation flow rate is calculated by means of the above equation (3).

Subsequently, it is possible to find a position corresponding to the target flow rate $Q_t$ by obtaining the rotational position of the dial 242 corresponding to the derived target gradation flow rate from the stored data and rotating the dial 242 to the position suitable therefor.

The above method of rotating the dial 242 of the flow rate regulator 240 to find the position corresponding to the target flow rate $Q_t$ may be used when the target flow rate $Q_t$ is small as well as when it is large.

However, when the target flow rate $Q_t$ is very small, it may be difficult to check whether the flow-rate regulator 240 is properly operated since the flow-rate regulator 240 must have a small passage and the time interval (or period) of falling drops may be a few seconds or more than several tens of seconds.

Accordingly, in order for the inventor to resolve the above-mentioned problems, secondly, the present invention uses a method of rotating the dial 242 at every time interval (or period) of falling the infusion solution drops for supply at a target flow rate $Q_t$ so that one drop falls to control the target flow rate $Q_t$.

Since the volume of one drop is known, a time interval (or period) of falling drops may be determined when the target flow rate $Q_t$ is given. When the time interval of falling drops is determined, the dial 242 is positioned at a position in which the drops to not fall and is rotated in the direction in which the passage is opened in time at which drops fall, thereby enabling a flow rate to be controlled while one drop falls. In this case, it is possible to control the flow rate by sufficiently rotating the dial 242 until one drop falls. Here, the falling of one drop uses the signal detected by the drop sensor 300.

Next, the dial 242 is rotated in the direction in which the passage is closed after one drop falls. In this case, the dial 242 may be rotated to a position in which the passage is fully closed, or may be rotated to any position in which drops do not fall at a time interval shorter than the time interval (or period) of falling drops corresponding to the target flow rate $Q_t$. The dial 242 is rotated in the direction in which the passage is opened until one drop falls at the next drop falling time, and then rotated in the direction in which the passage is closed. That is, the target flow rate $Q_t$ is controlled while the falling of the drops is controlled by rotating the dial 242 at every time corresponding to a desired time interval (or period) of falling drops.

This flow control method can be used with more convenience when the target flow rate $Q_t$ is small because the passage is fully opened such that drops easily fall in time at which the drops fall and the passage is fully closed again after the drops fall.

The above-mentioned first method and the second method of controlling the rotation of the dial whenever drops fall may be selectively used as occasion demands on the basis that the user of the infusion flow-rate regulating device 100 considers a target flow rate $Q_t$.

In addition, the second flow control method may be used to check whether the infusion solution set is normally set by setting the infusion solution set and then checking that drops fall while rotating the dial 242 of the flow-rate regulator 240 in the direction in which the passage is opened.

The infusion flow-rate regulating device 100 of the present invention may include a bubble sensor 125 or a temperature sensor as occasion demands.

The bubble sensor 125 is a sensor for detecting whether bubbles are generated in fluid flowing through the tube 220 and is provided to stop injection of an infusion solution when the bubbles are generated. Since the bubbles may be generated even by air in the internal passage of the flow-rate regulator 240, the bubble sensor 125 may be provided in the lower tube 220b connected to the outlet 241b of the flow-rate regulator 240.

The temperature sensor (not shown) is a sensor for detecting the temperature of fluid flowing through the tube 220 and may be installed on the outer peripheral surface of the tube 220 in the infusion solution set 200.

The controller 170 is electrically connected to the drop sensor 300 and the drive motor (not shown) capable of adjusting an angle of rotation and a direction, and may perform an initialization mode for selecting information used to control a flow rate, a flow control mode for controlling a flow rate at a target flow rate, and a monitoring mode for monitoring a flow rate after controlling the flow rate at a target flow rate.

Next, the operating mode of the infusion flow-rate regulating device according to the present invention will be described in detail.

The initialization setting mode includes a step of mounting the flow-rate regulator 240 to the infusion flow-rate regulating device 100 by the user. First, the dial 242 of the flow-rate regulator 240 is positioned at an initial position for blockage of injection, and the flow-rate regulator 240 is fixed by the dial mounting unit 130, the upper and lower mounting portions 121 and 122, and the flow-rate regulator separation unit 140, as described above.

After the drop sensor 200 is mounted to the drip chamber 210, a target flow rate $Q_t$ is input to the input unit 150. In this case, the type of the flow-rate regulator 240 and the type of the drip chamber 210 may be additionally selected as occasion demands, and thus the correlation information between the rotational position of the dial 242 to the selected flow-rate regulator 240 and the flow rate and the characteristic information on the selected drip chamber 210 are received from the controller 170.

When the target flow rate $Q_t$ is input, the controller 170 controls a flow rate of the infusion according to the selected control method.

First, the use of the above-mentioned second control method of rotating and controlling the dial 242 whenever each drop falls will be described.

When the target flow rate $Q_t$ is input, the controller 170 calculates a time interval (or period) of falling drops and displays it on the output unit 160. In this case, the correlation of a drop volume to a drop rate, a gradient, a temperature, or the like may be loaded together. If the types of the flow-rate regulator 240 and the drip chamber are selected, the selected correlation is loaded together. Next, by driving the drive motor (not shown), the dial 242 is rotated in the direction in which the passage is opened such that one drop falls, and then rotated in the direction in which the passage is closed. This process is repeated at the next drop falling time to control the target flow rate $Q_t$.

Next, the use of the above-mentioned first method of finding the rotational position of the dial 242 corresponding to the target flow rate $Q_t$ will be described.

When the target flow rate $Q_t$ is input, the controller 170 adjusts the dial 242 to an arbitrary initial rotational position by driving the drive motor (not shown). Here, the arbitrary initial rotational position may be preset or be a rotational position corresponding to the overall flow coefficient C or the gradation flow rate 242b equal to the target flow rate $Q_t$.

The controller 170 may select whether to use the overall flow coefficient C or the gradation flow rate 242b according to the item selected through the input unit 150 in the initialization setting mode to load data corresponding thereto, and may load the correlation between the flow rate and the rotational position to provide for the flow control mode. In this case, the correlation of a drop volume to a drop rate, a gradient, a temperature, or the like may be loaded together. If the types of the flow-rate regulator 240 and the drip chamber are selected, the selected correlation is loaded together.

The initialization setting mode may include a process of discharging air present in the internal passage of the tube 220 or the flow-rate regulator 240 by maintaining the dial 242 of the flow-rate regulator 240 at a maximum flow rate for a predetermined time. For example, when an air discharge menu is selected through the input unit 150, the dial 242 is adjusted to a maximum flow rate to be maintained for a preset time so as to discharge air, and is then rotated to blockage of injection. Subsequently, the following flow control mode is performed.

The flow control mode is a mode performed when the user inputs a target flow rate $Q_t$ through the input unit 150 after the initialization setting mode. In the flow control mode, when a target flow rate is input, an actual flow rate $Q_m$ is calculated based on the drop interval (or period) detected by the drop sensing part 330 after the motion sensing part 340 determines whether the drip chamber 210 vibrates and the dial 242 is rotated to an initial rotational position by driving the drive motor (not shown) when the vibration is not generated. Subsequently, the drive motor (not shown) is driven such that the dial 242 is adjusted to a target rotational position, which is the rotational position corresponding to the target flow rate, by the correlation of the flow rate to the rotational position of the dial 242.

The signal detected by the drop sensing part 330 of the drop sensor 300 is a signal indicative of a falling drop. Therefore, the controller 170 may calculate an actual flow rate $Q_m$ by calculating a drop rate from the drop interval (or period) and multiplying the drop rate by a drop volume, or may calculate an actual flow rate $Q_m$ by selecting a drop volume corresponding to the drop rate and/or the temperature of the infusion solution. That is, it is possible to accurately calculate the actual flow rate by reflecting the drop volume changed depending on the drop rate and/or the temperature of the infusion solution.

In this case, the actual flow rate $Q_m$ may be calculated from one drop rate (or drop interval) or may be calculated from an average drop rate (or average drop interval) through the number of preset continuous drops or the number of drops within a preset time. When the average drop rate is obtained, typically the number of preset drops may be determined within a range of 2 to 5 or may be determined more than 5 according to the drop rate or the like. Even though the actual flow rate $Q_m$ is calculated using the average drop rate, there is a need for a time until multiple set drops fall only when a primary average drop rate is calculated. From the second time, a new falling drop is included, except for the primary drop, and a new average drop rate is calculated. Therefore, it is possible to calculate the new average drop rate whenever one drop falls without the delay of time.

The target rotational position is derived by applying to the equation (1) or (3) according to when the overall flow coefficient C or the gradation flow rate is used as described above.

In this flow control mode, it is possible to set the flow rate, at which a fluid is administered to the infusion solution set 200, as a target flow rate $Q_t$ by measuring an actual flow rate $Q_m$ once and then adjusting the rotational position of the dial 242 of the flow-rate regulator 240 once.

Next, the monitoring mode is a mode for measuring and monitoring a flow rate at normal times or at every preset period after the flow control mode. When the acceleration measured by the motion sensing part 340 between a falling drop and a drop does not exceed a preset threshold at normal times or at the time of arrival of the present period, the controller 170 measures an actual flow rate using the motion sensing part 330 and displays it on the output unit 160. When the difference $\Delta Q$ between the measured actual flow rate $Q_m$ and the target flow rate $Q_t$ is greater than a preset value, the target rotational position may be readjusted to a position corresponding to the target flow rate $Q_t$ by the correlation of the flow rate to the rotational position of the dial 242. The acceleration may be selected as a vertical or horizontal component or an acceleration absolute value, and the acceleration threshold may be preset in the controller 170 or input as any value.

The acceleration threshold is set as a value at which the acceleration has a small influence on the drop interval (or period). That is, the acceleration value, at which the drop rate is changed as the drop interval (or period) is changed due to generation of only vibration in the drip chamber without the change of other conditions and thus the change of the calculated actual flow rate $Q_m$ is not required to be corrected, for example, the acceleration value, which is calculated that a flow rate change of 5% may occur or, when more precise administration is required, a flow rate change of 3% or 1% may occur, may be set as a threshold. In another way, the acceleration value, at which the vibration angle of the drip chamber does not exceed a certain angle in typical vibration such as when only vibration is generated in the drip chamber without external shocks or when walking, may be set as a threshold. In addition, the set value of the flow rate difference $\Delta Q$ may be preset in the controller 170 or input as any value. In this case, the value of the flow rate difference $\Delta Q$ may be determined within a range in which a patient is treated or recovered or is not at risk even though it is changed compared to the prescribed flow rate of the infusion. For example, the value of flow rate change of 10% or, when more precise administration is required, the value of flow rate change of 5% or 3% may be set as a threshold.

The rotational position of the dial may be readjusted using the overall flow coefficient C by readjusting the target rotational position of the dial in such a manner that the current position of the dial 242 is set as the initial rotational position of the dial 242 for obtaining an actual flow rate $Q_m$, in which case the measured flow rate is set as the actual flow rate $Q_m$. In addition, the rotational position of the dial may be readjusted by calculating the target rotational position corresponding to the target flow rate $Q_t$ using the correlation of the flow rate to the rotational position of the dial 242 as in the case of using the gradation flow rate.

The flow rate Q is changed when the level difference H is changed and/or when the dial 242 is operated from the outside, and thus the rotational position of the dial is readjusted for injection of an infusion solution at target flow rate ($Q_t$).

Meanwhile, the measured flow rate may be temporarily changed when the acceleration exceeding a preset threshold occurs in the infusion solution bag 10 or the drip chamber 210 due to vibration, shocks, or the like. Because this situation is temporary, the control of the flow rate regulator 240 may be rather erroneous as well as being useless. Therefore, in the present invention, drops measured while being subject to temporary disturbance are excluded from information for control and these drops are sorted as follows.

If a drop falls within a preset short time t as the acceleration equal to or greater than a threshold occurs instantaneously, the drop may be a drop falling before the drop has a normal volume by being affected by external additional vibration or shocks before it grows normally. This drop may be regarded as a drop subject to temporary disturbance. In this case, the preset short time t may be set as a specific value, or may be set as a value shorter than the drop period calculated by calculating the drop rate according to the target flow rate. On the other hand, if a drop does not fall within the preset short time t even though the acceleration equal to or greater than a threshold occurs instantaneously, the drop may be a drop falling after it grows to have a normal volume. Therefore, this drop may not be regarded as a drop subject to temporary disturbance.

Accordingly, when the acceleration measured by the motion sensing part 340 between a falling drop and a drop exceeds a preset threshold, the controller 170 of the present invention does not use the drop falling within the preset short time t in excess of the preset threshold to calculate an actual flow rate $Q_m$ and allows the previous flow rate to be displayed as it is on the output unit 160. On the other hand, the controller 170 determines that the drop falling after elapse of the preset short time t in excess of the preset threshold is a normal drop and uses the drop to calculate an actual flow rate $Q_m$.

Meanwhile, the number of drops, the drops not being used for flow rate detection, may exceed a preset number in unit time, which means an abnormal situation that acceleration equal to or greater than a threshold occurs frequently. In this case, since it is difficult to inject the infusion solution into a patient with a prescribed dosage, a user is informed of a current abnormal situation through a warning sound and/or a warning light and/or a warning message from the output unit 160 to take a measure.

Finally, although the acceleration has a value less than or equal to a threshold when a patient is sleeping or maintains one posture for a long time, injection of an infusion solution may be performed while the drip chamber 210 is maintained in a static inclined state. The flow rate is sometimes measured considering a change in drop volume upon the degree of inclination since the drop volume may be changed depending on the inclination of the drip chamber 210. Thus, the controller 170 of the present invention is configured to store a change in drop volume to the gradient of the drip chamber 210 as data and to correct the gradient at the time of calculation of an actual flow rate considering the change in drop volume to the gradient when the acceleration measured by the motion sensing part 340 between a falling drop and a drop does not exceed a threshold and the gradient is maintained within a preset difference $\Delta\theta$ at a specific value.

In this monitoring mode, the administered flow rate is kept constant at a target flow rate by adjusting the position of the dial 242 once for injection of an infusion solution at the target flow rate even when the installation of the infusion solution set is changed during injection of the infusion solution.

When a reset is input to the controller 170 through the input unit 150, the controller 170 controls the drive motor to adjust the dial 242 to a position for blockage of injection for termination of injection of the infusion solution. The reset may be performed in different manners. For example, the controller 170 may be configured to receive a total dosage through the input unit 150 and to adjust the dial 242 to a position for blockage of injection when the flow rate detected by the drop sensor 300 is added to reach the total dosage while performing the monitoring mode. Alternatively, the controller 170 may be configured to receive a total administration time, instead of the total dosage, through the input unit 150 and to adjust the dial 242 to a position for blockage of injection when an administration time is checked at the time of beginning of the monitoring mode to reach the total administration time.

Meanwhile, when the bubble sensor 125 detects that bubbles are generated more than a certain level while the flow control mode and the monitoring mode are performed, a user may be informed through a warning sound and/or a warning light and/or a warning message from the output unit 160 and simultaneously perform the reset operation, i.e., adjust the dial 242 to a position for blockage of injection.

While the present invention has been described with respect to the embodiments, it will be understood by those skilled in the art that various modifications may be made without departing from the spirit and scope or essential features of the invention. Therefore, it should be understood that the embodiments described above are for purposes of illustration only and are not intended to limit the scope of the present invention.

The scope of the present invention is defined by the appended claims, and it should be construed that all modifications or variations derived from the meaning, scope, and equivalent concept of the claims fall within the scope of the invention.

REFERENCE SIGNS LIST

10: infusion solution bag, 100: infusion flow-rate regulating device, 110: main body, 111: dial mounting unit installation part, 112: flow-rate regulator separation unit guide, 113: unlocking protrusion guide, 113a: latch groove, 114, 115: upper and lower guide, 116: auxiliary protrusion guide, 116a: elastic body support guide, 117: rotary plate, 118: coupling portion, 119: stepped portion, 121: upper mounting portion, 122: intermediate mounting portion, 123: fixed protrusion, 124: lower mounting portion, 125: bubble sensor, 130: dial mounting unit, 131: bottom, 132: mounting unit side, 133: side irregularity, 134: bottom irregularity, 135: fastening groove, 140: flow-rate regulator separation unit, 141: flow-rate regulator separation unit body, 141a: body flange, 142: locking bar, 143: support slope, 144: separation slope, 145: support groove, 146: unlocking protrusion, 146a: body, 146b: button installation portion, 146c: flange, 146d: button, 146e: stopper, 147: elastic body, 147a: elastic body support, 148: auxiliary protrusion, 149: flange seating part, 149a: coupling hole, 150: input unit, 160: output unit, 170: controller, 200: infusion solution set, 210: drip chamber, 211: insertion needle, 212: drop, 220: tube, 220a, 220b: upper and lower tube, 230: injection needle, 240: flow-rate regulator, 241: body, 241a, 241b: upper and lower tube connection, 241c: handle, 241d: reference protrusion, 242: dial, 242a: calibration, 242b: gradation flow rate, 242c: dial irregularity, 242d: initialization calibration, 250: roller clamp, 300: drop sensor, 310: first body, 311: first groove, 312: protrusion, 320: second body, 321: second groove, 322: elongated hole, 330: drop sensing part, 331: light emitting element, 332: light receiving element, 340: motion sensing part, 350: calculation unit, 360: elastic body, H: level difference, $H_m$: actual level difference, Q: flow rate, $Q_m$: actual flow rate, $Q_t$: target flow rate, C: overall flow coefficient, $C_m$: actual overall flow coefficient, $C_t$: target overall flow coefficient

INDUSTRIAL APPLICABILITY

The present invention relates to an infusion flow-rate regulating device available in the industry.

The invention claimed is:

1. An infusion flow-rate regulating device for rotating a dial of a flow-rate regulator to control a flow rate of an infusion, the infusion flow-rate regulating device comprising: a main body equipped with a drive motor therein; a dial mounting unit connected to the drive motor to mount and rotate the dial of the flow-rate regulator, wherein the dial mounting unit is rotatably connected to the main body; a flow-rate regulator separation unit capable of separating the flow-rate regulator which is mounted on the dial mounting unit from the main body; and a controller, wherein the flow-rate regulator separation unit comprises a hollow flow-rate regulator separation unit body rotatably connected to the main body, and wherein the flow-rate regulator separation unit body is provided in a front of the dial mounting unit such that the dial is mounted on the dial mounting unit after the dial passes through the flow-rate regulator separation unit body.

2. The infusion flow-rate regulating device according to claim 1, wherein the main body is further provided with an input unit and an output unit, and the controller is configured to derive a target rotational position of the dial, corresponding to an input target flow rate $Q_t$, from an equation of $Q=C \cdot H$ representing a relationship between a flow rate Q, a level difference H, and an overall flow coefficient C varied with the rotation of the dial of the flow-rate regulator.

3. The infusion flow-rate regulating device according to claim 2, wherein the controller is configured to measure an actual flow rate $Q_m$ at normal times or at every preset period to display it on the output unit and to readjust the target rotational position of the dial by means of a correlation between the rotational position of the dial, the actual flow rate $Q_m$, and the target flow rate $Q_t$ when acceleration of a drip chamber of an infusion solution set connected to the flow-rate regulator is less than or equal to a preset threshold and a difference $\Delta Q$ between the measured actual flow rate $Q_m$ and the target flow rate $Q_t$ is greater than a preset value.

4. The infusion flow-rate regulating device according to claim 2, wherein when acceleration of a drip chamber of an infusion solution set connected to the flow-rate regulator exceeds a preset threshold, the controller is configured such that a drop falling within a preset time tin excess of the acceleration threshold is not used to calculate an actual flow rate $Q_m$, thereby maintaining a previous flow rate $Q_m$ to be displayed on the output unit, whereas a drop falling after elapse of the preset time tin excess of the acceleration threshold is used to calculate the actual flow rate $Q_m$.

5. The infusion flow-rate regulating device according to claim 4, wherein when a count of drops not being used for detection of the actual flow rate $Q_m$ exceeds a preset number in unit time, the controller is configured to inform of it through a warning sound and/or a warning light and/or a warning message.

6. The infusion flow-rate regulating device according to claim 1, wherein the main body is further provided with an input unit, and the controller is configured to derive a time interval between two consecutive infusion solution drops corresponding to an input target flow rate $Q_t$, to rotate the dial of the flow-rate regulator at every time interval until one drop falls, and to rotate the dial in reverse after the next drop falls.

7. The infusion flow-rate regulating device according to claim 1, wherein the controller is configured to measure an infusion solution drop rate and calculate an actual flow rate $Q_m$ by multiplying the drop rate by a drop volume.

8. The infusion flow-rate regulating device according to claim 1, wherein the controller is configured to store volume change data of drop according to an infusion solution drop rate and/or a temperature of the infusion solution and to correct an actual flow rate $Q_m$ at the time of calculation of the actual flow rate $Q_m$.

9. The infusion flow-rate regulating device according to claim 1, wherein the controller is configured to store a relationship between changes in drop volume to a gradient of a drip chamber of an infusion solution set connected to the flow-rate regulator as data and to correct an actual flow rate $Q_m$ by reflecting the data at the time of calculation of the actual flow rate $Q_m$ when acceleration of the drip chamber between falling drops does not exceed a threshold and the gradient is maintained within a preset difference $\Delta\theta$ at a specific value.

10. The infusion flow-rate regulating device according to claim 1, wherein the flow-rate regulator separation unit body further comprises:
    support grooves formed in respective upper and lower portions; and
    a locking means for preventing arbitrary separation of the flow-rate regulator mounted on the dial mounting unit; and
    wherein the locking means comprises a locking bar formed in a front of each of the support grooves.

11. The infusion flow-rate regulating device according to claim 1, wherein the flow-rate regulator separation unit body further comprises:
    support grooves formed in respective upper and lower portions; and
    an unlocking means for separating the flow-rate regulator from the dial mounting unit; and
    wherein the unlocking means comprises an unlocking protrusion protruding from one side of the flow-rate regulator separation unit body.

12. The infusion flow-rate regulating device according to claim 11, wherein the unlocking protrusion comprises a button formed with a stopper capable of preventing the flow-rate regulator separation unit body from being arbitrarily unlocked.

13. The infusion flow-rate regulating device according to claim 1, wherein the flow-rate regulator separation unit body further comprises:
    support grooves formed in respective upper and lower portions; and
    a separation means for applying a force in a direction in which the flow-rate regulator is separated from the dial mounting unit, and
    wherein the separation means comprises a separation slope formed at one side within each of the support grooves.

* * * * *